United States Patent
Bonge, Jr.

(10) Patent No.: US 10,349,631 B2
(45) Date of Patent: Jul. 16, 2019

(54) WIRELESS ANIMAL TRAINING, MONITORING AND REMOTE CONTROL SYSTEM

(71) Applicant: Nicholas Jay Bonge, Jr., Ventura, CA (US)

(72) Inventor: Nicholas Jay Bonge, Jr., Ventura, CA (US)

( * ) Notice: Subject to any disclaimer, the term of this patent is extended or adjusted under 35 U.S.C. 154(b) by 0 days.

(21) Appl. No.: 14/599,233

(22) Filed: Jan. 16, 2015

(65) Prior Publication Data
US 2016/0021506 A1 Jan. 21, 2016

Related U.S. Application Data

(60) Provisional application No. 62/027,217, filed on Jul. 21, 2014.

(51) Int. Cl.
*A01K 3/00* (2006.01)
*G06F 8/65* (2018.01)
(Continued)

(52) U.S. Cl.
CPC ............ *A01K 29/005* (2013.01); *A01K 3/005* (2013.01); *A01K 11/008* (2013.01); *A01K 15/02* (2013.01); *A01K 15/021* (2013.01); *A01K 15/022* (2013.01); *A01K 15/023* (2013.01); *A01K 27/006* (2013.01); *A01K 27/009* (2013.01); *A63B 24/0062* (2013.01); *G01S 19/14* (2013.01); *G01S 19/16* (2013.01); *G06F 8/65* (2013.01); *G06F 8/656* (2018.02); *G06F 19/00* (2013.01); *G06F 19/3418* (2013.01); *G08B 21/182* (2013.01); *G08C 17/02* (2013.01); *G16H 40/67* (2018.01); *H04W 4/027* (2013.01); *H04W 4/12* (2013.01); *A63B 2024/0065* (2013.01); *G01S 19/49* (2013.01); *H04M 1/7253* (2013.01); *H04W 4/80* (2018.02); *H04W 76/14* (2018.02); *H04W 84/12* (2013.01)

(58) Field of Classification Search
CPC ...................................................... H04W 4/027
USPC ........................................................ 717/173
See application file for complete search history.

(56) References Cited

U.S. PATENT DOCUMENTS 5,724,025 A 3/1998 Tavori
5,927,233 A 7/1999 Mainini et al.
(Continued)

FOREIGN PATENT DOCUMENTS

WO WO 2008/112065 A1 9/2008
WO WO 2013/082407 A1 6/2013

OTHER PUBLICATIONS

International Search Report and Written Opinion for related International Application No. PCT/US2015/041202; dated Oct. 9, 2015; 8 pages.
(Continued)

*Primary Examiner* — Duy Khuong T Nguyen
*Assistant Examiner* — Theodore E Hebert
(74) *Attorney, Agent, or Firm* — Lewis Roca Rothgerber Christie LLP

(57) ABSTRACT

A method of updating firmware on a wireless animal communication system and communicating by the system including locating and downloading new firmware and wireless transferring to a device for the animal and send message in real time from the device for the animal to external devices.

24 Claims, 27 Drawing Sheets

(51) Int. Cl.

| | |
|---|---|
| *A01K 29/00* | (2006.01) |
| *A01K 27/00* | (2006.01) |
| *A01K 15/02* | (2006.01) |
| *A01K 11/00* | (2006.01) |
| *G06F 8/656* | (2018.01) |
| *G08B 21/18* | (2006.01) |
| *A63B 24/00* | (2006.01) |
| *H04W 4/02* | (2018.01) |
| *H04W 4/12* | (2009.01) |
| *G01S 19/16* | (2010.01) |
| *G01S 19/14* | (2010.01) |
| *G08C 17/02* | (2006.01) |
| *G06F 19/00* | (2018.01) |
| *G16H 40/67* | (2018.01) |
| *H04W 76/14* | (2018.01) |
| *H04W 4/80* | (2018.01) |
| *G01S 19/49* | (2010.01) |
| *H04M 1/725* | (2006.01) |
| *H04W 84/12* | (2009.01) |

(56) References Cited

U.S. PATENT DOCUMENTS

| | | | |
|---|---|---|---|
| 6,478,736 | B1 | 11/2002 | Mault |
| 6,720,879 | B2 | 4/2004 | Edwards |
| 6,874,447 | B1 | 4/2005 | Kobett |
| D570,237 | S * | 6/2008 | Goetzl .......... D30/152 |
| 7,467,603 | B2 | 12/2008 | Davies |
| 7,562,640 | B2 * | 7/2009 | Lalor .......... 119/719 |
| 8,823,524 | B2 | 9/2014 | Bradley et al. |
| 8,839,744 | B1 * | 9/2014 | Bianchi et al. .......... 119/720 |
| 8,868,796 | B1 * | 10/2014 | Wojcik et al. .......... 710/8 |
| 2003/0122677 | A1 * | 7/2003 | Kail, IV .......... 340/573.1 |
| 2004/0019289 | A1 | 1/2004 | Ross |
| 2004/0061606 | A1 | 4/2004 | Gronvold |
| 2005/0257752 | A1 * | 11/2005 | Langer .......... 119/712 |
| 2005/0263106 | A1 * | 12/2005 | Steinbacher .......... 119/858 |
| 2006/0202818 | A1 * | 9/2006 | Greenberg .......... 340/539.13 |
| 2006/0270421 | A1 * | 11/2006 | Phillips et al. .......... 455/457 |
| 2007/0100513 | A1 * | 5/2007 | Asano .......... 701/2 |
| 2007/0103296 | A1 | 5/2007 | Paessel et al. |
| 2007/0107668 | A1 * | 5/2007 | Eaton et al. .......... 119/719 |
| 2007/0184823 | A1 * | 8/2007 | Okkonen et al. .......... 455/419 |
| 2007/0204804 | A1 * | 9/2007 | Swanson et al. .......... 119/721 |
| 2008/0246656 | A1 * | 10/2008 | Ghazarian .......... 342/357.07 |
| 2010/0045463 | A1 * | 2/2010 | Bradley et al. .......... 340/573.1 |
| 2012/0052879 | A1 * | 3/2012 | Wildon et al. .......... 455/456.1 |
| 2012/0252430 | A1 * | 10/2012 | Imes et al. .......... 455/418 |
| 2012/0252486 | A1 * | 10/2012 | Lopez et al. .......... 455/456.1 |
| 2013/0014706 | A1 * | 1/2013 | Menkes .......... 119/859 |
| 2013/0185563 | A1 * | 7/2013 | Djabarov .......... G06F 9/44 713/176 |
| 2013/0227540 | A1 | 8/2013 | Ruster et al. |
| 2013/0321159 | A1 * | 12/2013 | Schofield et al. .......... 340/573.3 |
| 2014/0232541 | A1 * | 8/2014 | Trenkle .......... G08B 25/10 340/539.13 |
| 2014/0317611 | A1 * | 10/2014 | Wojcik et al. .......... 717/168 |
| 2015/0053144 | A1 | 2/2015 | Bianchi et al. |

OTHER PUBLICATIONS

International Search Report and Written Opinion for related International Application No. PCT/US2015/041193; dated Oct. 23, 2015; 13 pages.

International Search Report for corresponding International Patent Application No. PCT/US2015/041200, dated Dec. 4, 2015 (10 pages).

* cited by examiner

WIRELESS ANIMAL TRAINING, MONITORING AND REMOTE CONTROL SYSTEM

CROSS-REFERENCE TO RELATED APPLICATION(S)

This Patent Application claims priority to and the benefit of U.S. Provisional Patent Application Ser. No. 62/027,217, filed on Jul. 21, 2014, entitled WIRELESS ANIMAL TRAINING, MONITORING AND REMOTE CONTROL SYSTEM, the entire content of which is hereby expressly incorporated by reference.

BACKGROUND

Conventional wireless dog training systems, commonly known as electric fence systems, use a transmitter to transmit radio signals to a dog collar in order to determine the dog's location. These systems can apply various stimuli to the dog via the dog collar in order to train the dog to not leave the electric fence perimeter. Electric fence systems typically operate in the 28 to 433 MHz range as allowed by the FCC or the regulatory agency of the particular county or region in which the system is used. Such systems typically have a fixed set of controls at the transmitter and a fixed number of outputs at the collar with no means to monitor the behavior of the animal or record the effect of the collar's outputs on the animal. The receiver used by such dog collars systems have no capability to send data back to a human operator.

Unlike in the electric fence industry, in the field of wireless mobile device technology, external devices exist that have the capability to send data back to a human operator. External devices, such as heart rate monitors, are capable of providing information regarding the human using the external device back to a wireless mobile device. There are several commercially available protocols that link external devices to a wireless mobile device in real time to provide information regarding the human operator. Such available protocols may include networked, point-to-point and cellular protocols, the most commonly used wireless protocols being BLUETOOTH and Wi-Fi. For example, wireless mobile devices may be linked via a wireless protocol to external fitness devices that contain human fitness monitoring inputs. A software application in the wireless mobile device analyses the data from the fitness device and provides a human user with information regarding the fitness of the human user that may be useful in structuring an exercise routine.

However, systems involving external devices and wireless mobile devices that relay information regarding the state of an animal, such as a pet, to the human user are far more limited in capabilities and scope, focusing primarily on the location of the animal. One current system uses a smart phone to display the location of an animal-worn device. Location information is determined by a GPS locator in the device and that information is communicated to the smart phone via a cellular network. Another similar system, designed to locate an animal via GPS and display the location with a smart phone, also communicates limited information related to the animal's movements such as the speed and distance the animal has traveled during a certain period of time. Such information is collected at the collar presumably from an accelerometer and from the GPS data stored in the animal-worn device and then transmitted to the smart phone via a cellular network at some later point in time.

Another system, designed to contain an animal within a predetermined boundary, uses high frequency radio frequency coupling of a base transceiver and animal-worn device. Two-way communication between the transceivers is primarily for the purpose of ranging between the transceivers using chirp spread spectrum techniques to determine the time of flight of the signal and therefore, the distance between the two devices. When the animal-worn device is at a distance from the base transceiver greater than a predetermined value, the animal automatically receives a corrective stimulus generated by the animal-worn device. Information available to the human user is limited to what can be surmised by the ranging data, such as number of times the animal has breached the boundary.

Another system is a trackable sticker that can be adhered to an item, such as car keys or a pet, and tracked with a mobile device application. The sticker transmits a signal via BLUETOOTH technology to a mobile device for the purpose of locating said item via Received Signal Strength Indication (RSSI). The mobile device application allows the human user to set an alarm if the item leaves a selected range or comes within a selected range.

Finally, there exists a system, developed by the current inventor, that uses an animal-worn collar to control animal devices via an ultrasonic control signal. (See Bonge, U.S. Pat. No. 5,872,516 and U.S. Pat. No. RE41,629.) This system provides a one-way communication from an animal-worn collar to a remote device but does not allow for the flow of data from the collar to the human operator.

Although these systems can be used for locating animals, there is a need for a system that allows communication between an animal-worn device and a wireless mobile device to facilitate two-way communication between a wireless mobile device and an animal-worn device whereby the animal-worn device has inputs and outputs allowing a human to send real-time training stimuli to the animal and/or to collect useful data in real-time from the animal-worn device.

It is also desirable to create a system and method for a human to establish communication with the animal-worn device for the purpose of training and conditioning the health and fitness of the animal. It is further desirable for the system to allow the human to change and redefine commands or outputs as necessary and to input information pertaining to the specific characteristics of the animal, such as species, breed, size, weight, age and the like. It is further desirable to integrate into an animal-worn device a device to allow an animal wearing the transceiver to control other apparatuses in said animal's environment, for example, an automatic pet door.

SUMMARY

Embodiments of the current invention provide a powerful tool for remotely training animals and/or monitoring different aspects pertaining to an animal, such as its behavior, health, fitness and environment. Embodiments provide a multi-functional animal-worn device capable of receiving and sending various inputs and outputs, respectively, from/to a wireless mobile device. For example, signals may be sent from the wireless mobile device to activate outputs at the animal-worn device and the animal-worn device may send back acknowledgement of signal receipt and confirmation that a certain function was successfully performed. The animal-worn device may also collect data pertaining to its inputs and wirelessly send it to the wireless mobile device. Embodiments of the animal-worn device may interact with software applications on the wireless mobile device to allow for a variety of functions, including, but not limited to, the transfer of commands or stimuli to the animal, the transfer of data regarding the animal or its environment to the wireless mobile device, and/or the transfer of instructions from the animal-worn device to an external device. The animal-worn device may include all or some of these various functions.

Commercially available wireless mobile devices used for the animal training and/or monitoring system may include a variety of known mobile devices that contain wireless communication functionality, such as smart phones and tablets. Commands, data and firmware may be sent to the animal-worn device from the wireless mobile device utilizing the mobile device's existing communication protocols. The communication protocol used may be, for example, point-to-point, networked or cellular communication protocols. Commonly used networked and point-to-point communication protocols include WiFi and BLUETOOTH, respectively. The most commonly used cellular communication protocol makes use of GSM (Global System for Mobile Communications) or CDMA (Code Division Multiple Access) protocols. Any of these protocols may facilitate one-way or two-way wireless communication between the human and the animal-worn device.

Making use of the wireless and application executing capabilities of commercially available wireless mobile devices and coupling such mobile devices to the animal-worn device, further embodiments provide an animal training and/or monitoring system that a human user may configure with incredible flexibility. Wireless mobile device applications may be specifically tailored to the needs of a particular individual or group, such as sportsmen, law enforcement or pet owners, and may be changed and updated by wirelessly modifying the animal-worn devices without the requirement of physical changes to the animal-worn devices. In some embodiments, wireless mobile device applications may be able to send alerts, such as via email, SMS, website postings (e.g., Facebook, Twitter, etc.) or instant messaging, alerting the user of the condition of the animal based on information received from the animal-worn device.

Some embodiments of the invention utilize the wireless capability of the animal-worn devices to allow the animal to control external devices. For example, some embodiments of the invention allow the animal to control remotely operated devices, such as pet doors or automatic feeders, via wireless communications protocols. Other embodiments may also (or alternatively) provide a system for animals to control remotely operated apparatus such as electronic fences, barriers and the like. Accordingly, the animal-worn device may use signals emitted by various external devices as data inputs or to control its outputs.

Embodiments of the current invention may include one or more inputs at the animal-worn device, including, for example, a transceiver to receive inputs from the wireless mobile device, a vibration sensor, a temperature sensor, an accelerometer, a microphone, an audio recorder, a heart rate monitor, a magnetometer, a GPS locator, an auxiliary radio receiver, a photosensor, a conductivity sensor, a humidity sensor, a water sensor, a gyroscope and a camera. Embodiments of the current invention may include one or more outputs at the animal-worn device, including, for example, a transceiver to send inputs to the wireless mobile device, a shock generator, a spray module, an audio processor, a tone generator, a speaker, a lamp, a vibration generator and an auxiliary radio transmitter. Although certain embodiments detailed herein describe various uses for the various inputs and outputs, these are merely a representative few of the numerous applications that these inputs and outputs that can provide within the scope of the invention.

Some embodiments of the invention allow the human operating the wireless mobile device to activate training stimuli to train and condition the animal using some of the above inputs and outputs. For example, some embodiments allow the human operator to control an animal's behavior, such as unwanted barking, or create a boundary to limit the animal's movement. Such embodiments may also keep track of data related to the training, such as the number of times a dog has barked during a certain period or the number of times the animal has come into the field of a proximity sensor.

Further embodiments monitor the animal's behavior or health and fitness. For example, embodiments may monitor the speed at which an animal is moving and/or the animal's body temperature, heart rate and other vital signs. Other embodiments may also monitor environmental data, such as temperature and precipitation.

The specific inputs and outputs of the animal-worn device allow for the functionality of these different embodiments, and any of the different inputs and outputs may be combined in the animal-worn device depending on the needs of the human operator. For example, a pet owner desiring to train his pet may only require animal-worn device with inputs and outputs that provide such functionality, whereas another pet owner desiring to train her pet and to monitor the health and fitness of her animal may require the inputs and outputs related to training and to monitor health and fitness. On the other hand, a law enforcement officer in a K9 unit or a disabled person with a guide dog may require a different set of functionality. Some embodiments of the current invention provide a wide range of functionality based on the inclusion of multiple inputs and outputs, allowing the human operator to choose which functions he would like to use.

Further embodiments of the invention facilitate a real-time data link between the wireless mobile device and a remote server having the capacity of complex data analysis. The server may modify the wireless mobile device application and may also modify firmware at the animal-worn device. These modifications may update the way that the wireless mobile device manipulates the animal-worn device's inputs and outputs, thus modifying the way in which the animal is monitored and controlled.

BRIEF DESCRIPTION OF THE DRAWINGS

Further features and advantages of the embodiments of the invention will become apparent from the following description taken in conjunction with the accompanying drawings.

DETAILED DESCRIPTION

FIGS. 1-5 provide examples of different methods and protocols by which an animal-worn device 1 may communicate with a wireless mobile device 4. The wireless mobile device 4 may be capable of communicating with the animal-worn device 1 by any combination of the following methods and protocols.

Figure 1:
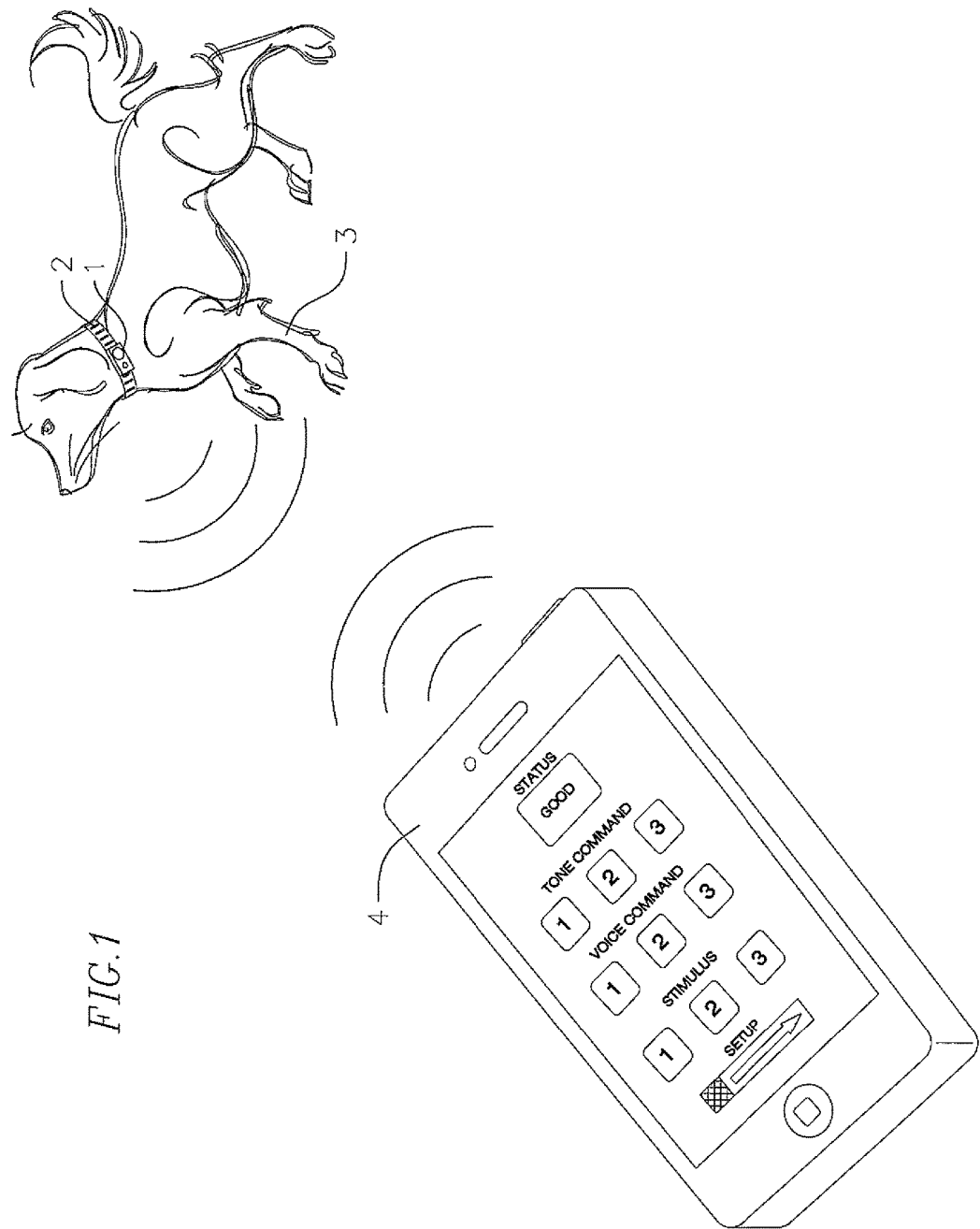
FIG. 1 shows an embodiment of the invention wherein a wireless mobile device communicates with an animal-worn device via a point-to-point wireless connection.

FIG. 1 shows the animal-worn device 1 wirelessly paired to the wireless mobile device 4 via a direct, point-to-point connection. The animal-worn device 1 may be affixed by means of flexible strap 2 to an animal 3. The wireless mobile device 4 wirelessly paired to the animal-worn device 1 may be a so-called smart phone or tablet with the capability of executing preprogrammed applications. Currently, the predominant devices with this capability utilize the iOS operating system proprietary to Apple Corporation or the Android operating system proprietary to Google. Other currently available operating systems include Blackberry and Windows. The current embodiment requires that the wireless mobile device 4 be capable of executing a preprogrammed application and be capable of wirelessly communicating with an external device. Many commercially available wireless mobile devices incorporate ancillary radio transceivers, separate from that used for cellular communication, for the purpose of exchanging data over relatively short distances. Such transceivers typically operate in the 2.4 gigahertz range and communicate via BLUETOOTH or WiFi protocols. Referring again to FIG. 1 the animal-worn device 1 includes a radio transceiver (see, e.g., transceiver 16 of FIG. 7, discussed below) using compatible frequencies and protocols to wirelessly communicate and exchange data with an ancillary transceiver of the wireless mobile device 4. For this purpose, the BLUETOOTH protocol is particularly useful because it is configured for direct one-to-one pairing. The BLUETOOTH Low Energy (BLE) protocol has the advantage of very low energy consumption per unit time while achieving practical ranges upward of 400 feet with future designs predicted to achieve working ranges upward of 2500 feet. WiFi has the advantage of being able to transmit and receive large amounts of data per unit of time making it practical for transmitting audio and video signals over approximately the same distance ranges as the BLUETOOTH devices with the disadvantage of higher energy consumption. In addition to WiFi and BLUETOOTH protocols, the radio transceiver of the animal-worn device 1 can be configured to wirelessly communicate and exchange data via other protocols at a variety of frequencies.

Figure 2:
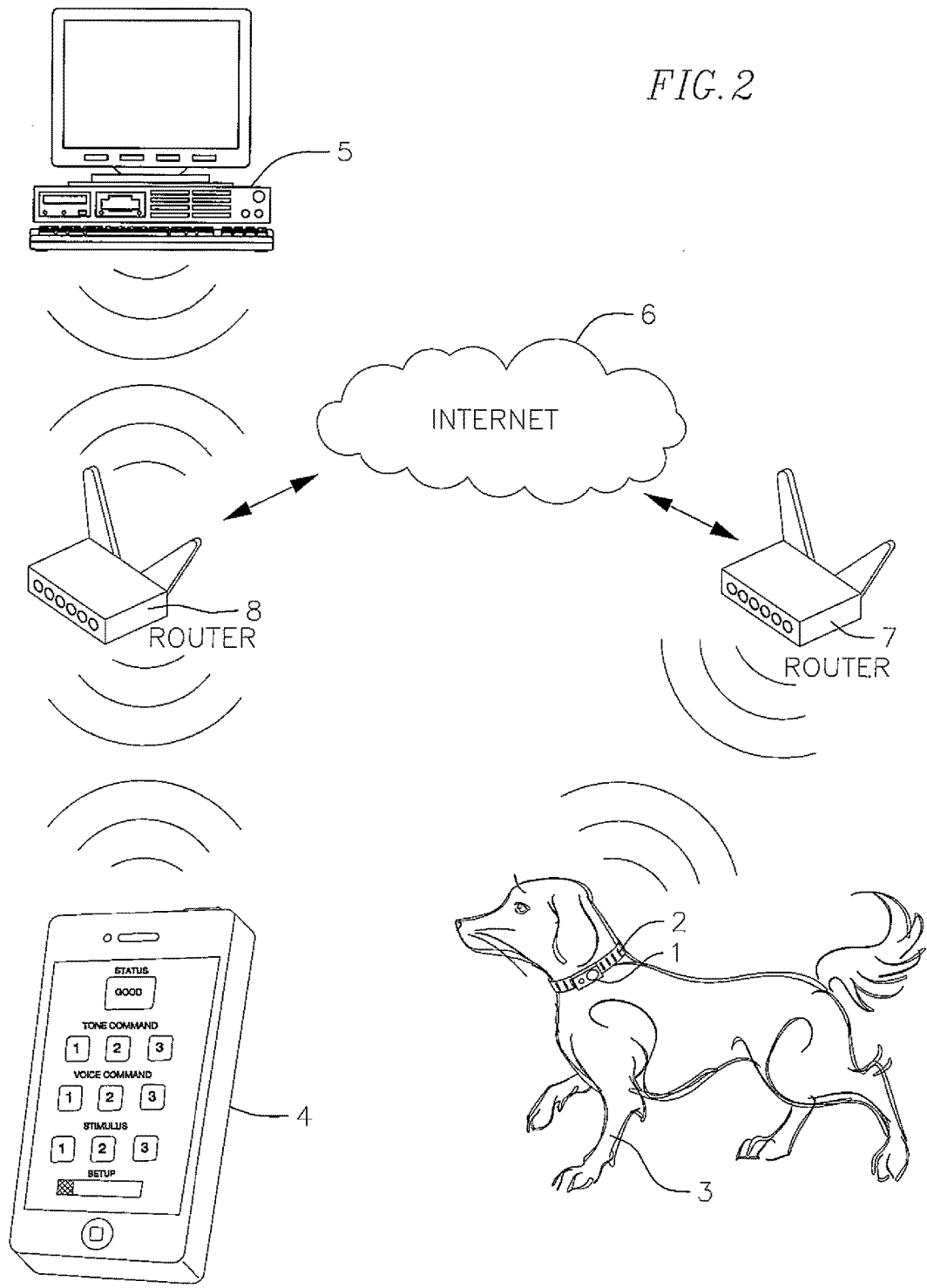
FIG. 2 shows an embodiment of the invention wherein a plurality of wireless computing devices communicates with the animal-worn device via wireless routers and the internet.

FIG. 2 shows an example of data being exchanged with the animal-worn device 1 via a wireless network. The network may include other programmable devices, such as personal computer 5. The animal-worn device 1 in this embodiment may also be capable of exchanging data via other methods, such as the previously discussed point-to-point connection. The animal-worn transceiver 1 may communicate with the personal computer 5 and the wireless mobile device 4 via wireless routers 7 and 8 and the internet using a communication protocol, such as IEEE 802.11 Wi-Fi. This allows a human to monitor and control the animal 3 remotely via a wide choice of devices, including the wireless mobile device 4. Wireless linking of the animal-worn device 1 to a wireless network such as WiFi may also be used to monitor and control the animal 3 at a long range. The animal-worn device 1 sends and receives wireless signals via wireless routers 7 and 8 which may be linked to the wireless mobile device 4. A human user may then, at considerable distance, communicate with the animal-worn device 1 via the internet 6.

Figure 3:
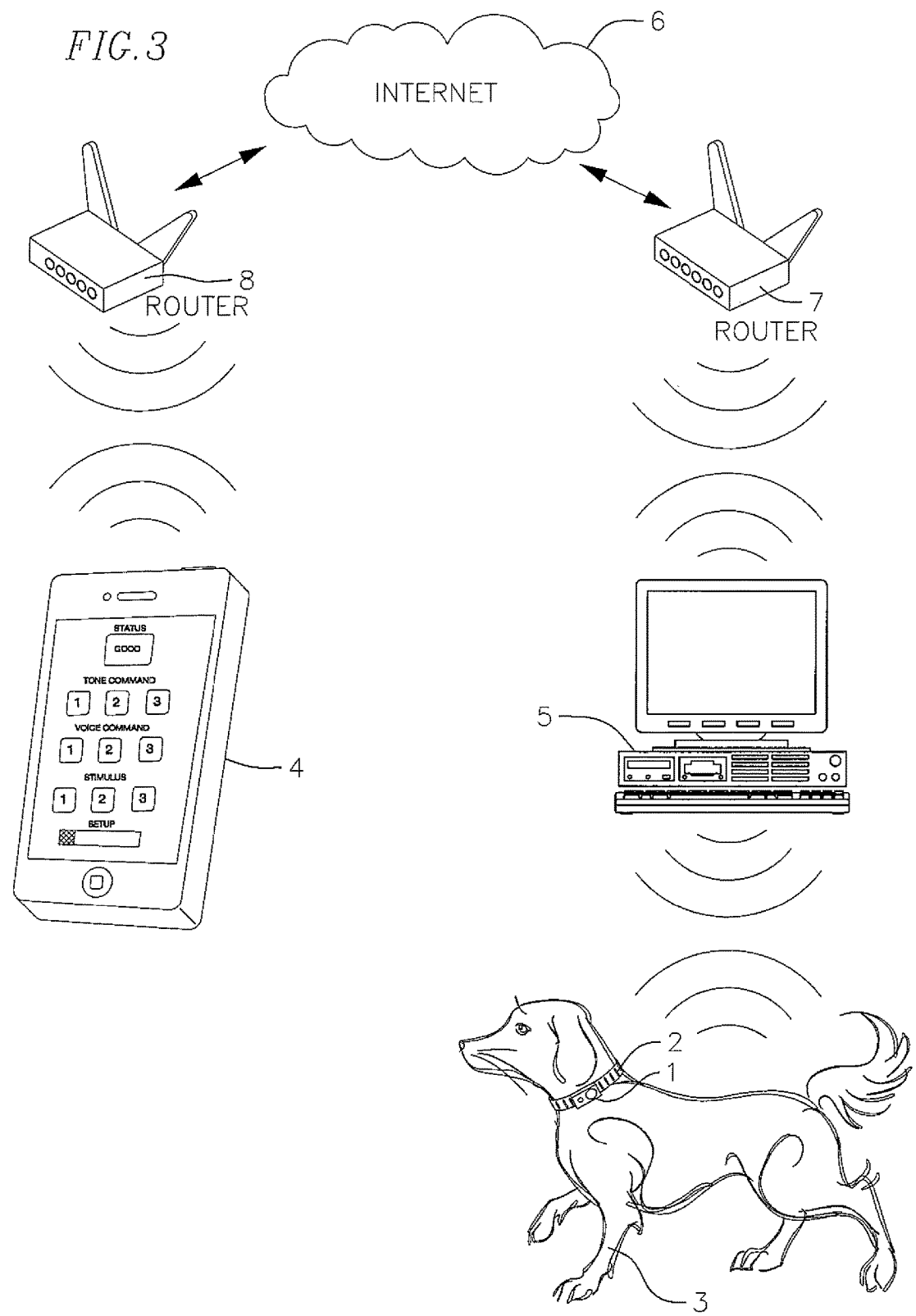
FIG. 3 shows an embodiment of the invention wherein the animal-worn device communicates wirelessly with a personal computer which in turn communicates with the wireless mobile device via wireless routers and the internet.

FIG. 3 shows an example of the animal worn device 1 communicating with the personal computer 5 via a protocol such as BLUETOOTH. This is advantageous since many commercially available personal computing devices include wireless capability, such as BLUETOOTH. The personal computer 6 communicates with other devices such as the wireless mobile device 4 via routers 7 and 8 and the internet. It is common for computing devices to connect to the internet wirelessly using the WiFi protocol. In a further embodiment, the animal-worn device 1 may use a low energy communication protocol, such as BLUETOOTH low energy BLE, while devices such as the personal computer 5 and the wireless mobile device 4 may take advantage of higher data rates from a more energy consumptive communication protocol, such as WiFi.

Figure 4:
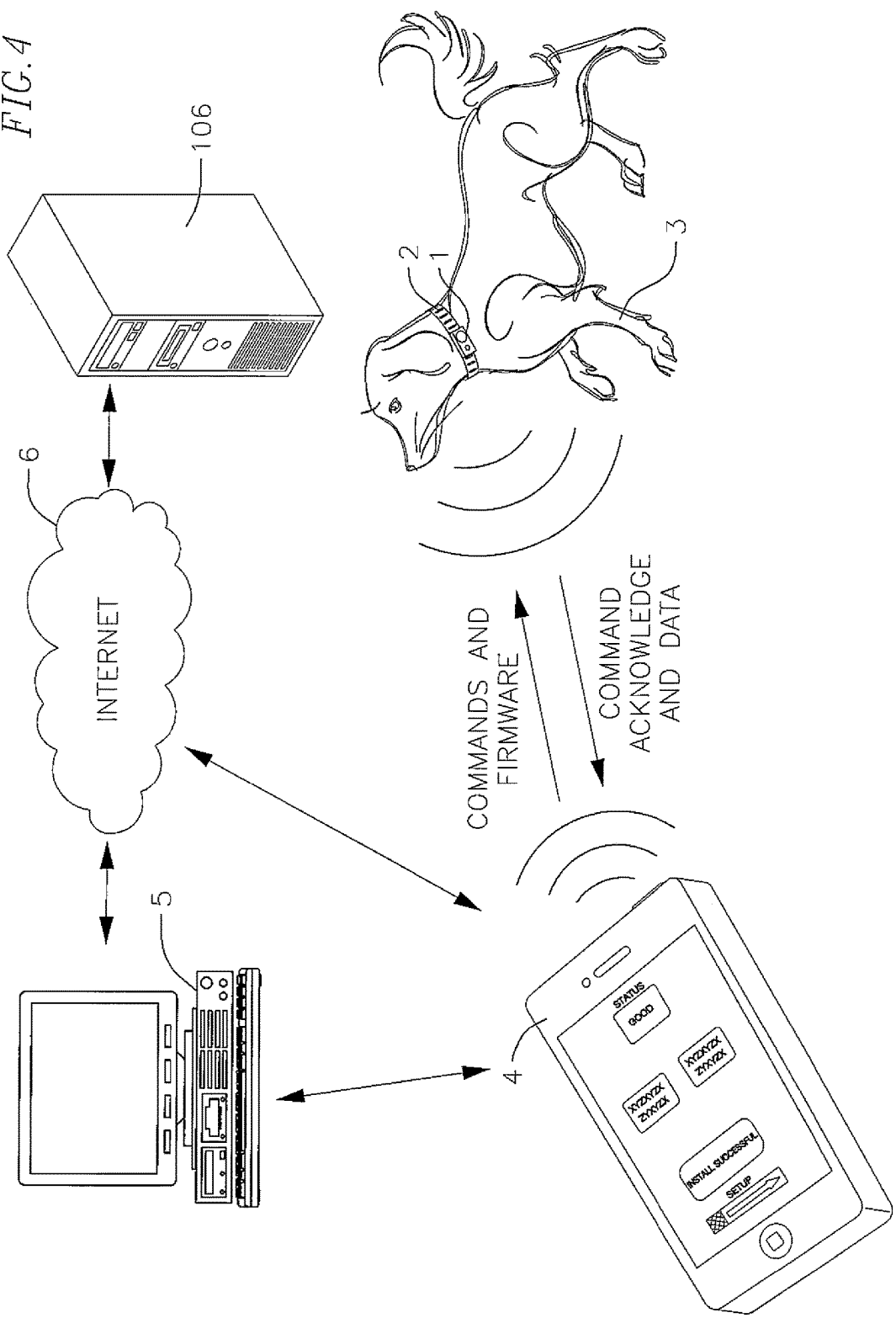
FIG. 4 shows an embodiment of the invention wherein the animal worn transceiver communicates wirelessly with the wireless mobile device which in turn communicates with the server and the personal computer via the internet.

FIG. 4 shows an example of data from the animal-worn device 1 being sent to the wireless mobile device 4 and relayed via the internet to a remote server 106. The remote server 106 may contain dynamic software that may send push messages to the wireless mobile device 4 or even tailor new firmware to be downloaded by the animal-worn device 1 based on the input data received. Indeed, the animal-worn transceiver 1 may acquire new software or firmware including input/output and data analysis programs from the wireless mobile device 4. As illustrated in FIG. 4, new firmware may be acquired wirelessly by the wireless mobile device 4 from the personal computer 5 or from the remote server 106 via the internet 6. In addition, connection to the internet 6 may allow the wireless mobile device 4 to send data collected at the animal-worn device 1 to the remote server 106, which may use more sophisticated programs to analyze the collected data and may send back useful messages to the wireless mobile device 4.

Figure 5:
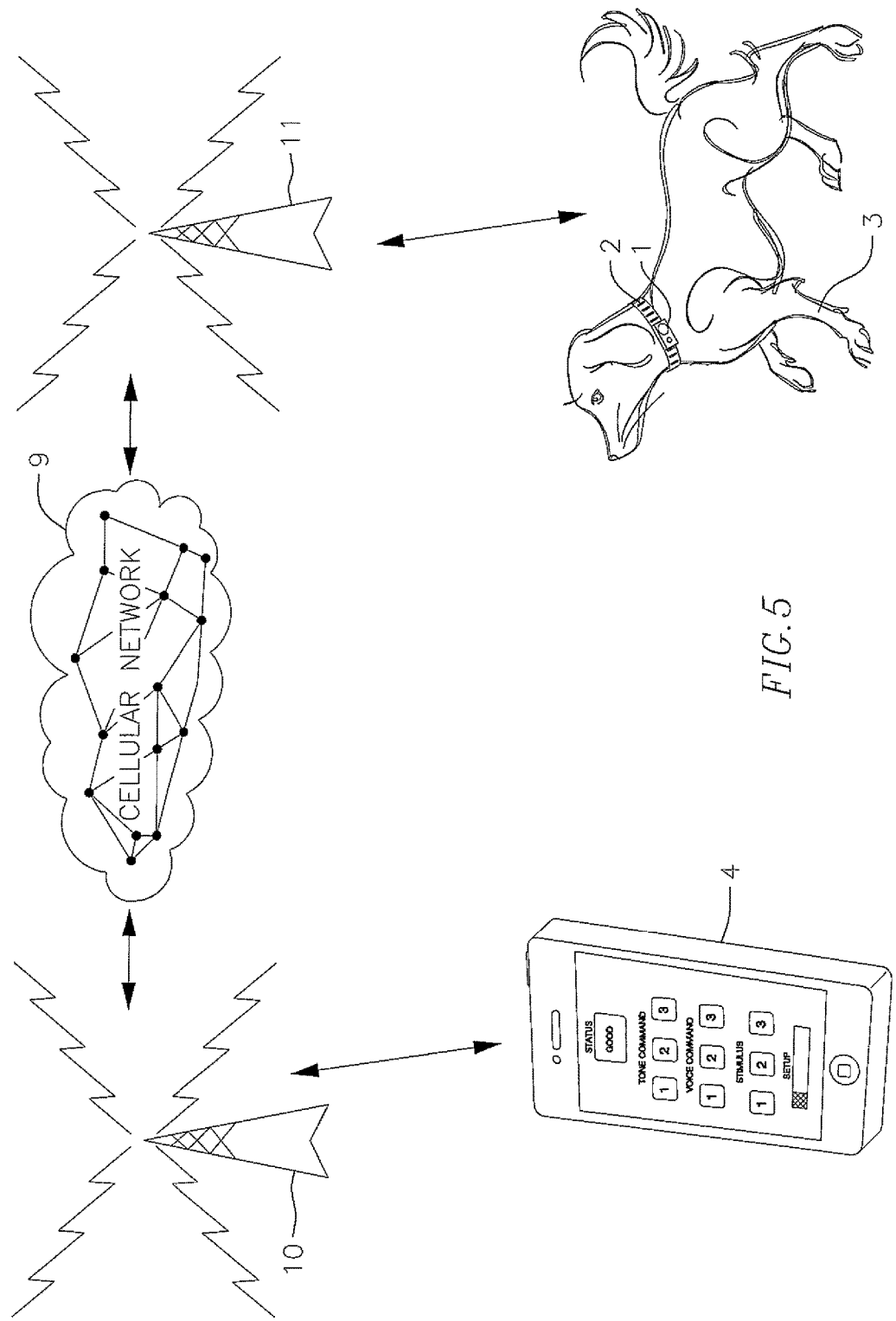
FIG. 5 shows an embodiment of the invention wherein the wireless mobile device communicates with the animal-worn device via a cellular network.

In the embodiment shown in FIG. 5, the animal-worn device 1 includes a wireless telephone receiver (see, e.g., antenna 14 of FIG. 7, discussed below), which communicates with the wireless mobile device 4 over a cellular network 9 by way of cellular communication towers 10 and 11, effectively allowing a human to monitor and control the animal 3 from any point on Earth that has access to a wireless telephone network, such as GSM (Global System for Mobile Communications), CDMA (Code division multiple access) or others. Linking the animal-worn device 1 and the wireless mobile device 4 via the cellular network 9 may allow the human user to call up the animal-worn device 1 and establish direct communication for the purpose of long range monitoring of the inputs and activation of the outputs at the animal-worn device 1 from any location that has cellular access. In this embodiment, the animal-worn transceiver 1 contains a cellphone transceiver 143, which may be accessed over the cellular network 9 by the wireless mobile device 4 whenever a human wishes to activate outputs or monitor inputs at the animal-worn device 1. Accordingly, the animal-worn device 1 may initiate communication with the wireless mobile device 4 when a particular input condition has occurred. For example, the animal-worn device 1 may initiate communication when a sensor (see, e.g., microphone 22 and audio recorder 23 of FIG. 7, discussed below) at the animal-worn device 1 detects that the animal 3 is barking excessively. The human user receiving the communication via the wireless mobile device 4 may then activate an output at the animal-worn device 1. For example, the human user may remotely trigger a training tone or electric shock stimulus, to correct the undesired behavior. Obviously, many other scenarios are encompassed by the current invention wherein outputs of the animal-worn device 1 may be monitored and controlled by the wireless mobile device 4 over the cellular network 9.

Once data exchange is established between the animal-worn device 1 and the wireless mobile device 4, a pre-programmed application (or applications) on the wireless mobile device 4 is employed to operate inputs and outputs at the animal-worn device 1 for purposes including training, containing and monitoring the behavior, health, physical fitness of animal 3 and/or monitoring and controlling selected devices in animal's 3 environment. The pre-programmed applications may be installed on the wireless mobile device 4 and embodiments of such applications are described below with reference to FIGS. 11-26.

Figure 6:
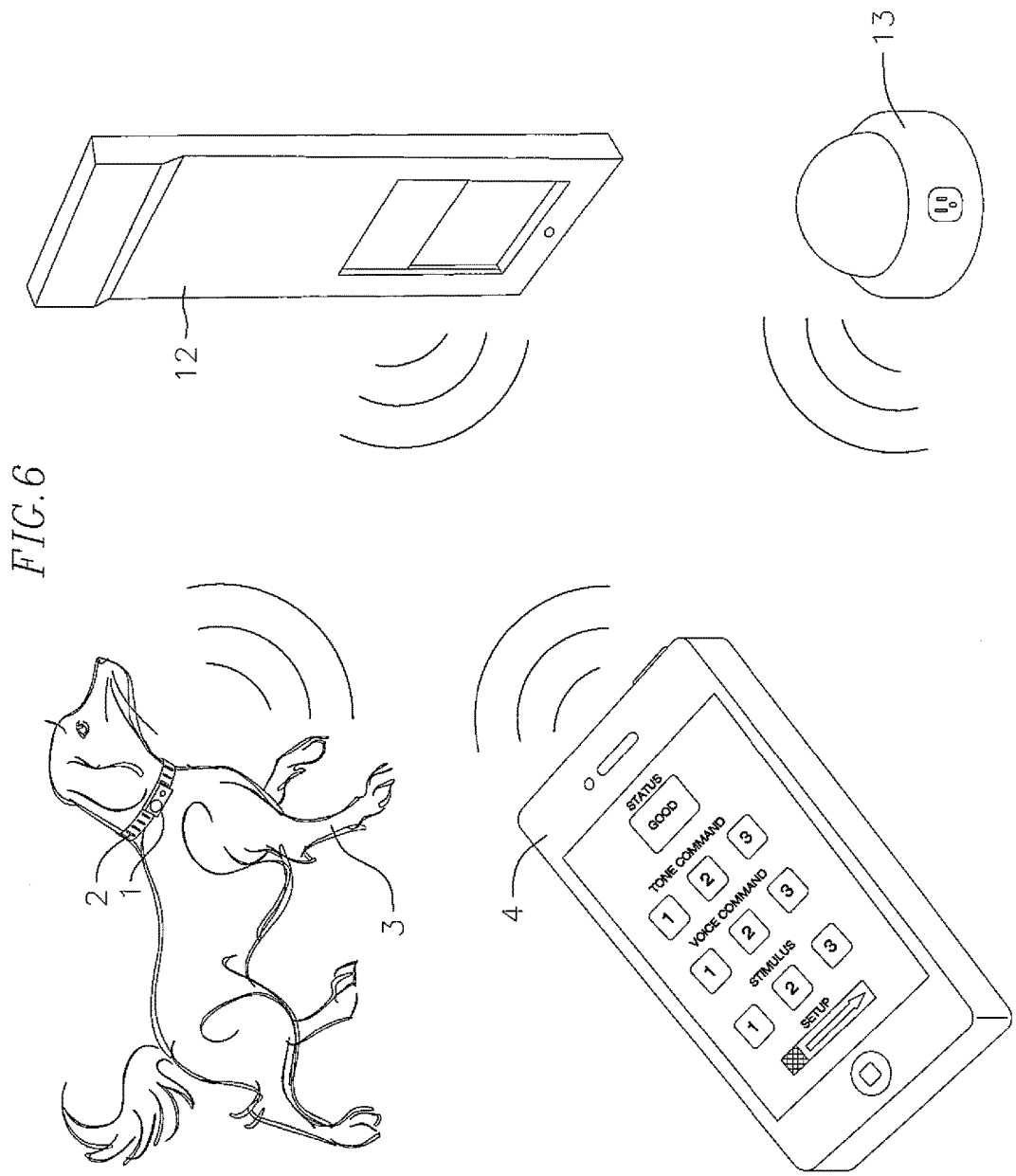
FIG. 6 shows the animal-worn device in wireless communication with external apparatuses.

FIG. 6 shows an embodiment wherein the animal-worn device 1 may communicate with at least one external apparatus for the purpose of remotely controlling that apparatus. For example, the animal-worn device 1 may control an automatic pet door 12, where the radio signal emitted by the animal-worn device 1 may cause the automatic pet door 12 to open, allowing the animal 3 to pass through whenever the animal-worn device 1 is within a predetermined distance. The distance can be determined, for example, by using the received signal strength of the animal-worn device's 1 wireless signal. Alternatively, a remote transceiver 13 may communicate with the animal-worn device 1 and detect when the animal 3 is within a predetermined distance using the received signal strength of the animal-worn device's 1 wireless signal or other ranging or proximity sensing techniques. The remote transceiver device 13 may then send a signal to the animal-worn device 1 instructing it to activate selected outputs according to a set of pre-programmed instructions. For example, the remote transceiver device 13 may be used as an area restriction device wherein it instructs the animal-worn device 1 to activate a shock output whenever the animal 3 comes within a predetermined distance. Alternatively, the remote transceiver device 13 may be used as a wireless fence device wherein it instructs the animal-worn device 1 to activate a shock output whenever the animal 3 goes outside of a predetermined distance. Data may be stored in the animal-worn device 1, such as the number of times the animal 3 has come within or left the predetermined distance. The data may be sent to the wireless mobile device 4 in real-time or at a later time via one of the communication protocols previously described. A software application on the wireless mobile device 4 may allow the data to be displayed on the wireless mobile device 4. This same software application, or a different application, on the wireless mobile device 4 may be used by the human operator to send inputs to the remote transceiver device 13. For example, the human user may input the predetermined distance in embodiments where the remote transceiver device 13 is used as an area restriction device or wireless fence.

The remote transceiver device 13 may also possess control device capably of controlling various appliances, such that those appliances may be switched on or off when the animal-worn device 1 is within a predetermined distance. The remote transceiver 13 may thereby, be pre-programmed to perform a plurality of useful tasks such as turning on the lights when the animal 3 enters the room, activating automated food or water dispensers and other useful apparatuses that may be used to automate the care and safety of the animal 3. Control of apparatuses may be digital, as in the case of turning lights off and on, or analog, for example setting the lights at a predetermined intensity level based upon the condition of certain of animal-worn transceiver inputs. The remote transceiver device 13 may also communicate with the wireless mobile device 4 or the other wireless devices previously described for dynamic control of the animal's 3 environment. For example, the remote transceiver 13 may receive instructions in real time from the wireless mobile device 4 or other wireless devices instructing it to turn on sprinklers or air conditioning when the animal's 3 temperature rises above a predetermined set point. For another example, the remote transceiver 13 may be instructed to turn on soothing music when the animal 3 is whining. A wide variety of pre-programmed tasks are possible using external devices wirelessly in communication with the wireless mobile device 4 and the animal-worn transceiver 1.

Figure 7:
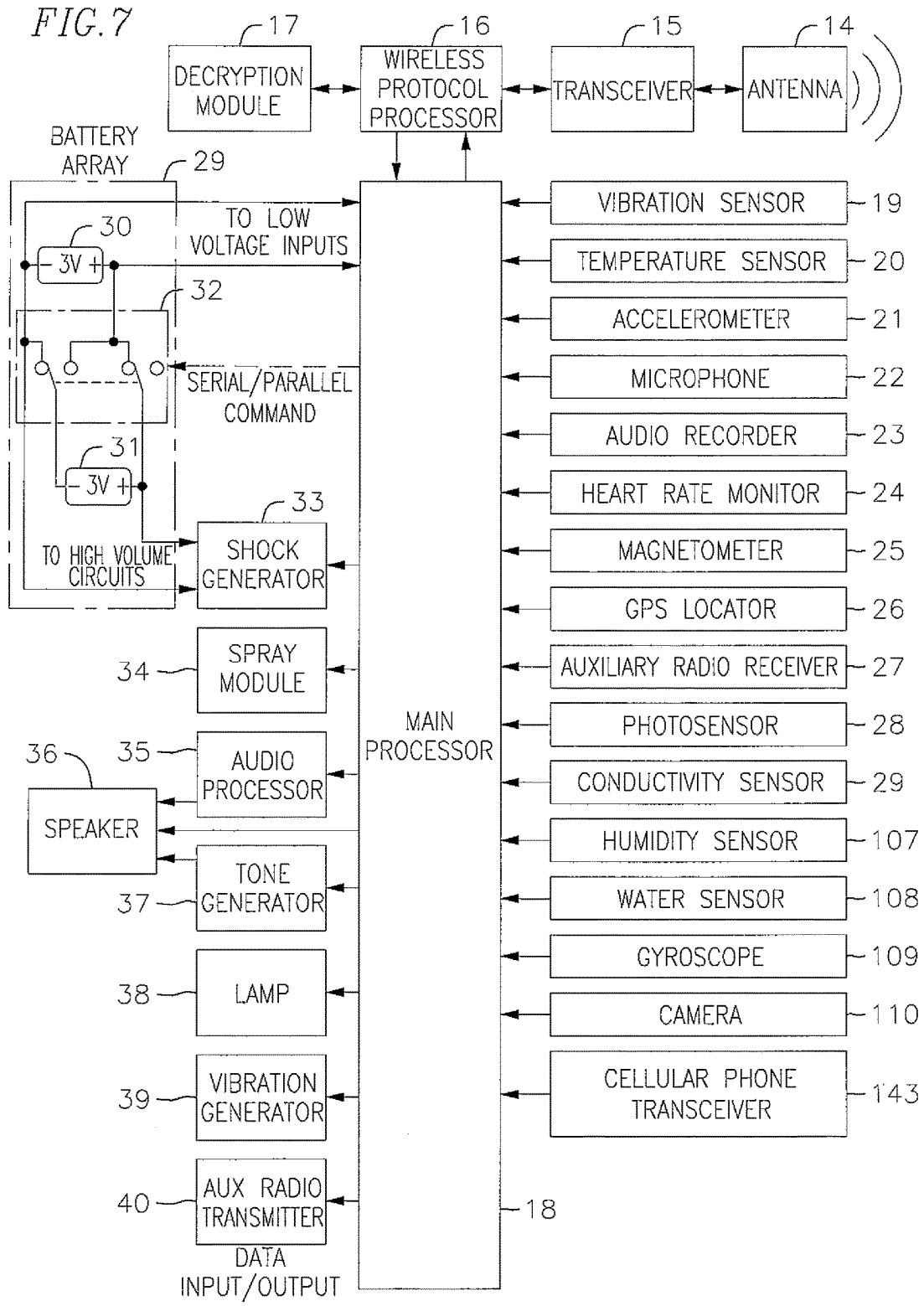
FIG. 7 is a block diagram of the animal worn transceiver.

FIG. 7 shows a block diagram of the animal-worn transceiver 1 and components that may be included in it. The animal-worn device 1 includes an antenna 14 or the like to send signals to and receive signals from the wireless mobile device 4, the wireless router 5 and/or the cellular network 9 as previously described. The animal-worn device 1 includes a transceiver 15, which contains at least one radio transceiver and may include a processor to modulate and condition incoming and outgoing signals. For example, a wireless protocol processor 16 may be included to condition signals to conform to the particular wireless protocol being used, such as BLUETOOTH, WiFi or other wireless protocols. There are currently commercially available integrated circuits which perform the functions of the antenna 14, the transceiver 15 and the wireless protocol processor 16 in a single chip that may be used in place of separate components. Such integrated circuits typically employ BLUETOOTH or WiFi protocols.

The animal-worn device 1 may also include a decryption module 17, which may be necessary for communicating with an operating system of a wireless mobile device that encrypts its wireless signals, such as is the case with many such mobile devices currently. Specifically, the decryption module 17 may be necessary to decrypt some communication modes of the Apple iOS operating system in order for the animal-worn device 1 to communicate with devices running that operating system.

The animal-worn device 1 includes a main processor 18 to control logic and input/output functions based upon pre-programmed instructions and external commands received from the wireless mobile device 4, the personal computer 5 and/or other external devices such as the remote transceiver device 13. The main processor 18 contains software allowing the animal-worn device 1 to communicate with one or more of the previously described wireless devices. It may also contain self-aware software that communicates directly with the previously described external devices and may activate outputs at the animal-worn device 1 according to pre-programmed instructions independent of or in tandem with an application contained in the wireless mobile device 4, the personal computer 5 and/or other wireless computing devices.

Reference numbers 19-29 and 107-110 are examples of input devices that may be included in the animal-worn device 1 to feed data to the main processor 18. The animal-worn device 1 may include one or more of these input devices. Information from an input device may be received by the main processor 18 and then output to the wireless mobile device 4, for example, via the wireless protocol processor 16. Reference numerals 33-40 are examples of output devices which may be integrated into the hardware of the animal-worn device 1 and controlled by the main processor 18. The animal-worn device 1 may include one or more of these output devices. Outputs may include information sent to these output devices from the main processor 18 and/or information sent from the main processor 18 to the wireless mobile device 4, for example, via the wireless protocol processor 16. It may not be necessary for all functions and inputs and/or outputs of the animal-worn device 1 to be operating at all times. When the animal 3 is at rest, for example, main processor 18 may shut down certain functions and/or input and output devices to reduce energy consumption.

Input devices that may be included in the animal-worn device 1 will now be discussed in detail with reference to FIG. 7.

The animal-worn device 1 may include a vibration sensor 19 to detect an utterance, such as a dog bark, made by the animal 3 by directly detecting the motion of the animal's 3 vocal cords. Such detection may be done alone or in tandem with a microphone 22. The animal-worn device 1 may include a temperature sensor 20 capable of measuring an ambient environmental temperature and/or the animal's 3 body temperature.

The animal-worn device 1 may include an accelerometer 21 to detect changes in the animal's 3 speed or direction of motion. The accelerometer 21 may incorporate a multi-axis and gyroscopic architecture that may be used to automatically activate selected outputs based upon the animal's speed and direction of motion. In a further embodiment, the accelerometer 21 may be used in conjunction with a GPS locator 26 and a gyroscope 109 to determine the location of the animal-worn transceiver 1 to a high degree of accuracy, especially when the main processor 18 is enhanced with software that uses data from the accelerometer 21 and the gyroscope 109 to compensate for GPS location error. Another embodiment uses the accelerometer 21 as a pedometer by detecting the movements of the animal-worn transceiver 1 along the vertical axis that are generated as the animal 3 takes steps. Each step creates a vertical oscillation that represents forward movement of the animal 3 that, when multiplied by the distance of the animal's 3 gate, provides a precise measurement of the distance of the animal's 3 forward movement. When mathematically divided by the time between each step, a precise measurement of animal's 3 velocity may also be determined. Of course, there are numerous other embodiments in which an onboard accelerometer may be useful.

The animal-worn device 1 may include a microphone 22 to detect an animal's utterance as a noninvasive alternative to using vibration sensor 19. Detection of such utterances may be useful in order to control unwanted sounds, such as barking, from the animal 3. For the purposes of dog bark detection, software in the main processor 18 may be installed that compares incoming audio signals from the microphone 22 with the audio voice characteristics of a typical dog bark. These audio voice characteristics may include frequency, pulse duration and amplitude. Even more sophisticated bark detection may be achieved by feeding the signal from the microphone 22 to the audio recorder 23 to record the audio waveform of animal's 3 bark. The audio waveform may then be digitally stored in the processor 18. The audio waveform of any subsequent incoming bark may then be compared to the stored audio waveform. If the two waveforms are determined by predetermined criteria to be substantially similar, the processor 18 may initiate a behavioral correction sequence using one or more of output devices 33-40. This technique effectively tunes the bark detection to the specific voice of animal 3. The microphone 22 may also be capable of detecting sounds in the environment of the animal 3 for any of a variety of purposes, including determining the location of the animal 3, should it become lost, or recording an audio history of the animal's 3 comings and goings by feeding its audio signals to audio recorder 23 and storing an audio record in the processor 18. The microphone 22 may also be capable of recording human voice. Such voice recordings may be used, for example, to directly record verbal audio commands to be used as outputs.

The animal-worn device 1 may include a heart rate monitor 24 to aid in monitoring the health of the animal 3 and may be used to assist the human user in properly exercising the animal 3. The heart rate monitor 24 may be integrated into the animal-worn device 1 or may be a separate external device to be worn by the animal 3, for example, as a harness.

The animal-worn device 1 may include a magnetometer 25 to measure changes in the Earth's magnetic field. Heading information from magnetometer 25 may be combined with roll and pitch data from the accelerometer 21 in the main processor 18 to calculate the exact orientation of animal-worn device 1 as it moves.

The animal-worn device 1 may include a GPS locator 25 to detect the position on the Earth of the animal-worn transceiver 1 using the Global Positioning System via communication with the GPS satellites. Alternate embodiments may use a GLONASS receiver to communicate with the GLONASS satellites in the same way. Such an input device is useful in tracking the whereabouts of animal-worn device 1 and accordingly the location of the animal 3. Combining data from the accelerometer 21, the magnetometer 25, the gyroscope 109 and the GPS locator 26 results in the ability to track and locate the animal-worn device 1 with a high degree of accuracy. Embodiments, such as the above, may be used to contain the animal 3 within certain boundaries or to track the general location of the animal 3.

The animal-worn device 1 may include an auxiliary radio receiver 26 such as a low frequency type radio receiver used to detect the position of the radio receiver relative to a wire loop boundary antenna for the purpose of animal containment. Alternatively, the auxiliary radio receiver 26 may be used to wirelessly generate an invisible boundary within which the animal 3 is to be contained.

The animal-worn device 1 may include a photo sensor 28 to detect the light level in the animal's 3 environment. In one embodiment, the main processor 18 may activate selected outputs in daylight and a different set of outputs at night based on the detected light levels from the photo sensor 28.

Figure 9:
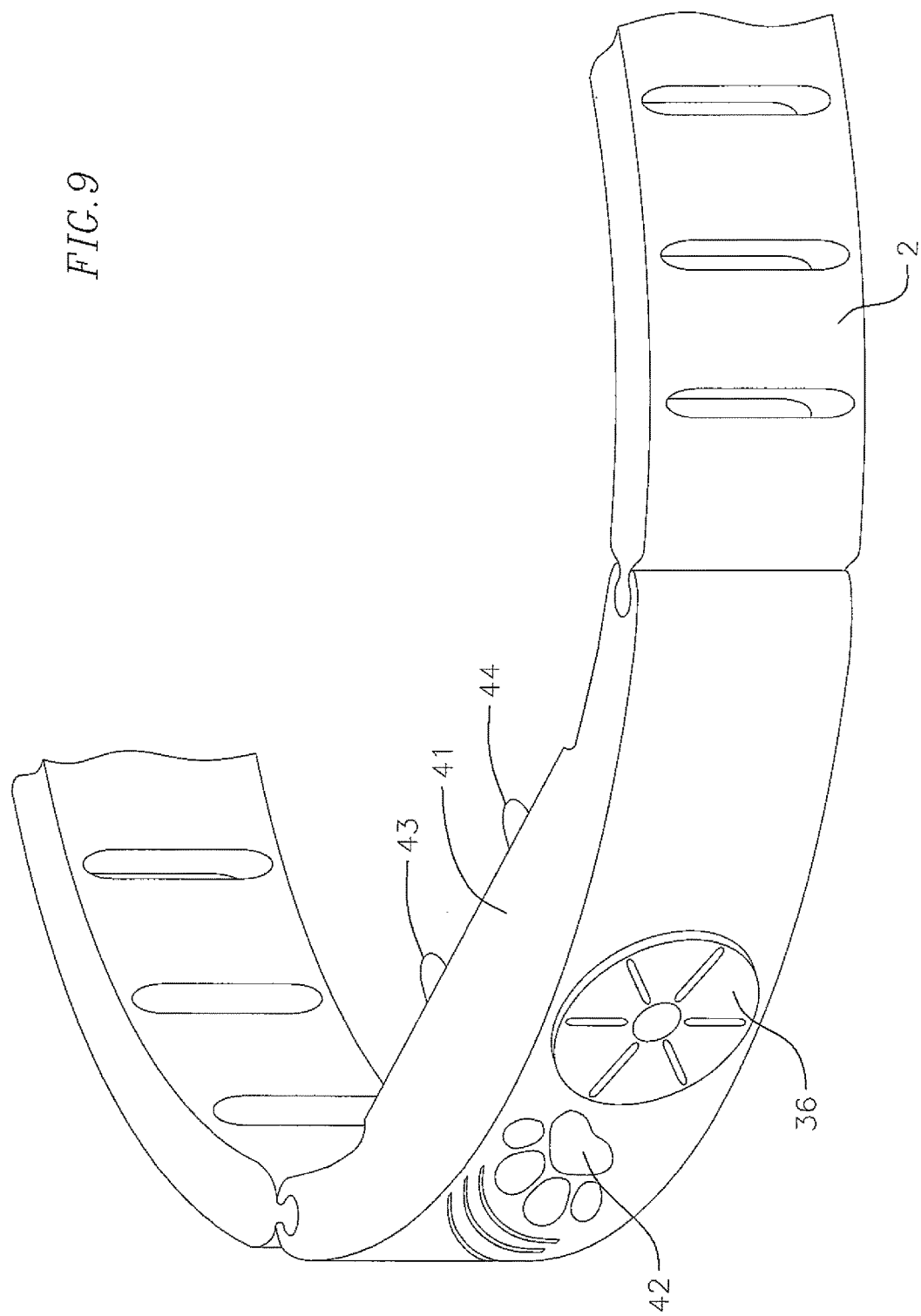
FIG. 9 is a perspective front view of the animal-worn device.
Figure 10:
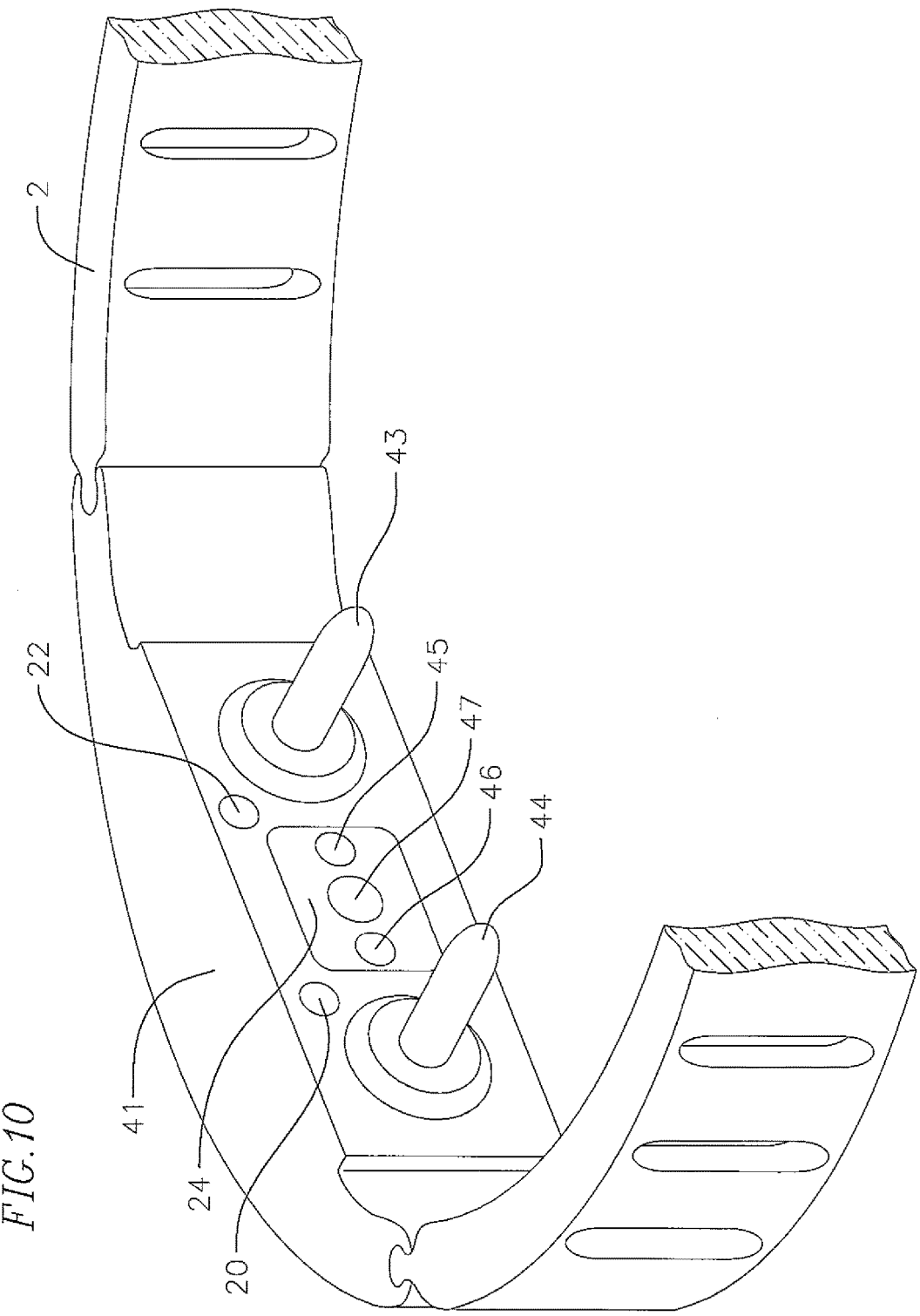
FIG. 10 is a perspective rear view of the animal worn transceiver of FIG. 9.

The animal-worn device 1 may include a conductivity sensor 29 to detect the electrical conductivity, impedance and/or capacitance between shock electrodes 43 and 44, as shown in FIGS. 9 and 10, in order to detect and insure that the electrodes 43 and 44 are making sufficient contact with the animal's 3 skin so that the animal 3 may receive the stimulus generated by a shock generator 33.

The animal-worn device 1 may include a humidity sensor 107 to detect ambient humidity for use in monitoring the animal's 3 environment. Data from the humidity sensor 107 may be incorporated into programs used in the wireless mobile device's applications related to the animal's 3 health and fitness. The animal-worn device 1 may also include a water sensor 108 to determine when the animal 3 is in a rainy environment or if animal 3 has immersed itself in water such as a pool, lake or ocean. This may be used in conjunction with the conductivity sensor 29 to determine if the animal is immersed in salt water.

As discussed above, the animal-worn device 1 may include the gyroscope 109 to detect the orientation of the animal-worn transceiver 1. The gyroscope 109 may be used to correctly interpret incoming wireless signals that may attenuate based upon the orientation of the animal-worn transmitter 1 relative to the axis of the emitted wireless signal waves. For example, the RSSI of a wireless signal typically varies greatly depending upon the relative orientation of the device receiving the wireless signal. Attenuation of RSSI based upon device orientation may be corrected using a gyroscope to more accurately measure distance between the emission source and the device.

The animal-worn device 1 may include a camera 110. The camera 110 may be a still image or video recording device for use in locating the animal 3 should it become lost or for use in creating a still image or video history of the animal's 3 comings and goings.

The animal worn device may include cellular phone transceiver 143 for allowing two-way communication over a cellular telephone network in place of or in addition to the wireless transceiver 15.

Output devices that may be included in the animal-worn device 1 will now be discussed in detail with reference to FIG. 7.

The animal-worn device 1 may include the shock generator 33, which generates electrical stimulus which may be used to get the attention of the animal 3 in order to correct undesirable behavior. The animal-worn device 1 may include a spray module 34 that may be used as an alternative corrective stimulus to spray a liquid or mist, such as citronella, which the animal 3 may find unpleasant but not painful. Alternatively, the spray module 34 may be used to create a positive reinforcing stimulus by spraying a mist that the animal 3 finds pleasant, for example steak aroma, when the animal 3 exhibits desirable behavior.

The animal-worn device 1 may include an audio processor 35 that receives audio-encoded electronic signals from the main processor 18 and translates the electronic signals into voice and music quality audio output for broadcast by a speaker 36. The animal-worn device 1 may include a tone generator 37 that receives audio-encoded electronic signals from the main processor 18 and translates the electronic signals into discrete audio tones for audio broadcast by the speaker 36. Alternatively, the tone generator 37 may activate a dedicated output device such as a piezoelectric transducer in place of the speaker 36. The audio tones generated by the tone generator 37 may be used by a person training the animal 3 to communicate specific commands to the animal 3. Each command may be associated with a discrete and unique audio tone.

The animal-worn device 1 may include a lamp 38 that provides light output used as a training stimulus, a status message to the human user, to illuminate the animal's 3 path at night or to locate the animal 3 in the dark. The animal-worn device 1 may include a vibration generator 39 that may consist of a small electric motor with an offset load at its rotation shaft to create vibratory stimulus to be used to train the animal 3. The animal-worn device 1 may include an auxiliary radio transmitter 40 that may be used for specialized purposes apart from the transceiver 15.

FIG. 7 also shows that the animal-worn device 1 includes a battery array 29 to provide power to the animal-worn device 1. Typically, the operating voltage required by commercially available microprocessors, such as may be used as the main processor 18, is lower than that required for other outputs employed by the animal-worn device 1. For example, the shock generator 33 may require significantly higher voltage than the main processor's 18 operating voltage. When operating both the main processor 18 and the shock generator 33 from a single battery, the voltage needed to operate the main processor 18 may need to be stepped down, resulting in energy loss and loss of practical battery life. Alternatively, operating the main processor 18 and the shock generator 33 from separate batteries is possible, but may be impractical if it requires the human user to replace two different batteries at different times, or if both batteries are contained in a single battery pack, it limits the useful battery life to that of the shortest lasting battery and wastes the energy of the unspent battery. To address this issue, the battery array 29 may include primary and secondary batteries 30, 31 and a switch 32. The primary battery 30 is sized to closely match the required processor operating voltage of the main processor 18, for example, 3 volts. The secondary battery 31 is sized so that when placed in series with the primary battery 30, the shock generator 33 is supplied with a higher, more optimum supply voltage. In this example, the secondary battery 31 is sized at 3 volts so that when in series with the primary battery 31, 6 volts is delivered to the shock generator 33. In practice, selecting batteries of equal voltage is preferable for many battery types, such as lithium batteries, however, different voltage batteries may be used. The switch 32, which in this embodiment is a DPDT switch, is operated by a series/parallel control signal provided by the main processor 18. With the switch 32 in its normal, non-activated, position, primary and secondary batteries 30, 31 are in parallel supplying 3 volts to both the low voltage and high voltage circuits, in this example, the main processor 18 and the shock generator 33. When the main processor 18 receives a command to activate the shock generator 33, it sends a control signal placing switch 32 in its activated position. This puts the primary and secondary batteries 30, 31 in series supplying 6 volts to the shock generator 33 while taking the secondary battery 31 out of the circuit supplying voltage to the main processor 18. In this state, 3 volts is supplied to the low voltage circuits (the main processor 18) while simultaneously 6 volts is supplied to the high voltage circuits (the shock generator 33). When the switch 32 is returned to its non-activated position both the primary and secondary batteries 30, 31 are placed in parallel and any difference in voltage between the two batteries caused by unequal current drain will quickly equalize. This power circuit allows the normal operating voltage of the animal-worn device 1 to be set at 3 volts with the ability to supply 6 volts as needed for momentary power to the high voltage circuits with zero losses typical of conventional step up-step down voltage techniques. This power circuit also facilies the use of components, such as a shock output transformer, which may be smaller in size and operate more efficiently than lower voltage counterparts. While the primary and secondary batteries 30, 31 each supply a voltage of 3 volts in this example, other voltages are possible based on the needs of the animal-worn device 1 and the main processor 18. Also, while this embodiment is discussed with reference to the shock generator 33, similar power circuits can also be connected to other output devices or input devices where a higher or lower voltage is needed.

Figure 8:
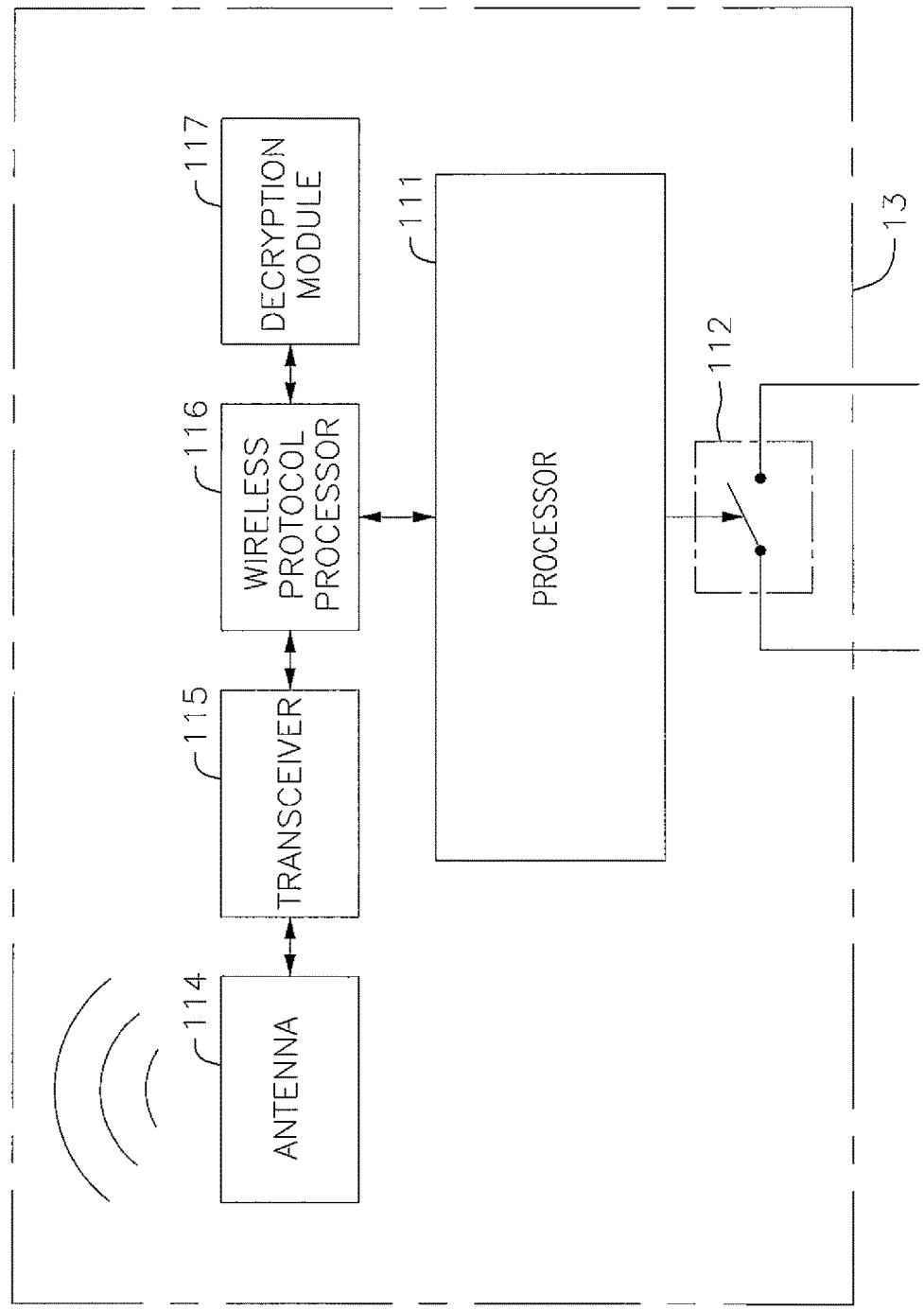
FIG. 8 is a block diagram of a remote transceiver device.

FIG. 8 shows a block diagram of the remote transceiver 13. An antenna 114, a transceiver 115, a wireless protocol processor 116 and a decryption module 117 are similar to the antenna 14, the transceiver 15, the wireless protocol processor 16 and the decryption module 17 of the animal-worn device 1. Processor 111 may contain pre-programmed logic to execute programs when the animal-worn device 1 comes within a predetermined distance. These programs may activate outputs at the animal-worn device 1 or change the state of a remote transceiver switch 112 from open to closed and vice versa. The remote transceiver switch 112 may thereby control other selected apparatuses that may be switch controlled, such as electric lights, automatic food dispensers, radios and the like. For example, the remote transceiver may be part of a pet door such as the automatic pet door 12 to control the opening and closing of the pet door 12 when the animal 3 is within the predetermined distance. Alternatively, an analog control device may be used in place of the switch 112 to control analog apparatuses.

FIG. 9 shows a perspective view of the animal-worn device 1 according to one embodiment. The animal-worn device 1 includes a casing 41 for housing the electronic components. A strap 2 is provided for attaching the device around the neck of the animal 3. In this embodiment, the shock electrodes 43 and 44 are provided for applying electrical stimulus generated by the shock generator 33 to the animal 3. The casing 41 may contain a decorative cut-out 42, which may be filled with a translucent material such as glass or clear plastic. The decorative cut-out 42 may be shaped in the form of a logo or other meaningful design. The lamp 38, as shown in FIG. 7, may be placed inside the casing 41 such that the light it emits will shine through the cut-out 42 and be visible to the human user. Although in this embodiment the cut-out is decorative, it may also be a non-decorative, simple and/or functionally-shaped cut-out. In one embodiment, the animal-worn device's 1 main processor 18 can activate the lamp 38 whenever a command is received from the wireless mobile device 4 or other remote activating device.

The speaker 36 may be enclosed within the casing 41 and positioned in front of an opening such that acoustical emissions may be transmitted through the air. The speaker 36 may be of the commercially available waterproof variety and may be sealed to the casing 41 so as to prevent water leaking into the casing 41 should the animal 3 decide to immerse itself in a body of water.

FIG. 10 shows a rear perspective view of the animal-worn device 1 of FIG. 9. As shown in FIG. 10, the animal-worn device 1 may include at least one temperature sensor 20 placed at the back side of the casing 41 to measure the animal's 3 body temperature. Additionally, at least one microphone 22 may be included to detect audible sounds uttered by the animal 3, by a human or other sounds from the environment. The heart rate monitor 24 may be included to detect the animal's 3 pulse rate by emitting light from a light source 47 and detecting the backscattering with light detectors 45 and 46 using a known process whereby blood vessels that contain a higher volume of blood absorb more light of certain frequencies than do blood vessels containing less blood. As blood pulses through the veins of the animal 3, backscattered light of certain frequencies will be detected with varying amplitude, the rise or fall of amplitude following the pulse rate of the animal 3 yielding a pulse rate equal to the heart rate of the animal 3. The resulting heart rate may be transmitted to the wireless mobile device 4 or stored in the main processor 18 for transmission at a later time. The heart rate of the animal 3 may be used by the wireless mobile device 4 in executing applications relating to the health and fitness of the animal 3.

Figure 11:
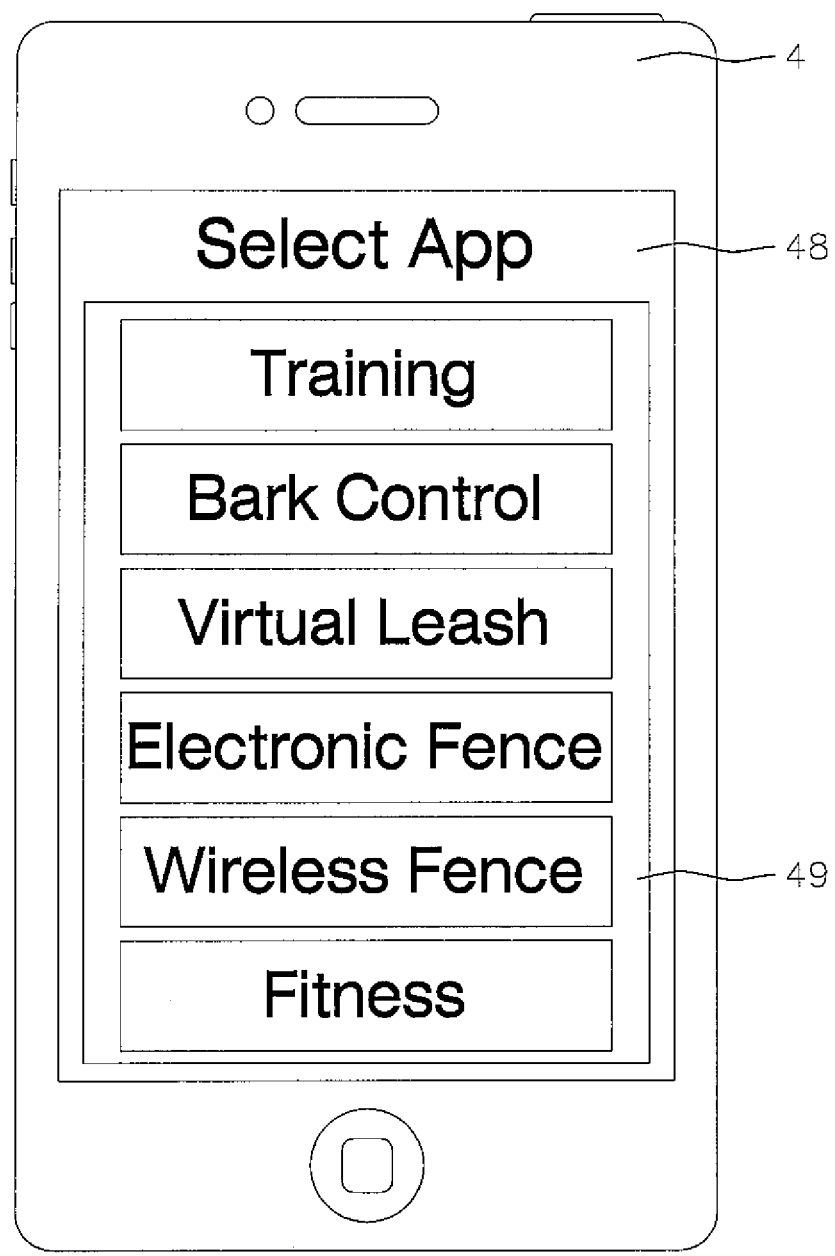
FIG. 11 shows the wireless mobile device with a display screen displaying a list of pre-programmed applications on the wireless mobile device.

FIG. 11 shows the wireless mobile device 4 with a display screen 48 displaying a list of pre-programmed applications that may be available for use when the wireless mobile device 4 is wirelessly paired to the animal worn device 1. The wireless mobile device 4 may include any number of applications such as these which work wirelessly with the animal-worn device 1. The listed applications, including "Training," "Bark Control," "Virtual Leash," "Electronic Fence," "Wireless Fence," and "Fitness," will be discussed in detail with respect to FIGS. 12-26 below. These and similar applications may also be subroutines that are all part of the same application on the wireless mobile device 4.

FIGS. 12-16 show graphical interfaces and a representational diagram of an embodiment of a "Training" application. The "Training" application uses point-to-point communication, via a protocol such as BLUETOOTH, between the wireless mobile device 4 and the animal-worn device 1 to allow the human user 68 to train and monitor the animal 3 in real time. The human user 68 may transmit training stimuli the animal wearing animal-worn device 1 while observing the animal in real time. Outputs at the animal-worn device 1 may include positive stimulation to encourage certain desired behaviors or negative stimulation to deter undesired animal behavior.

Figure 12:
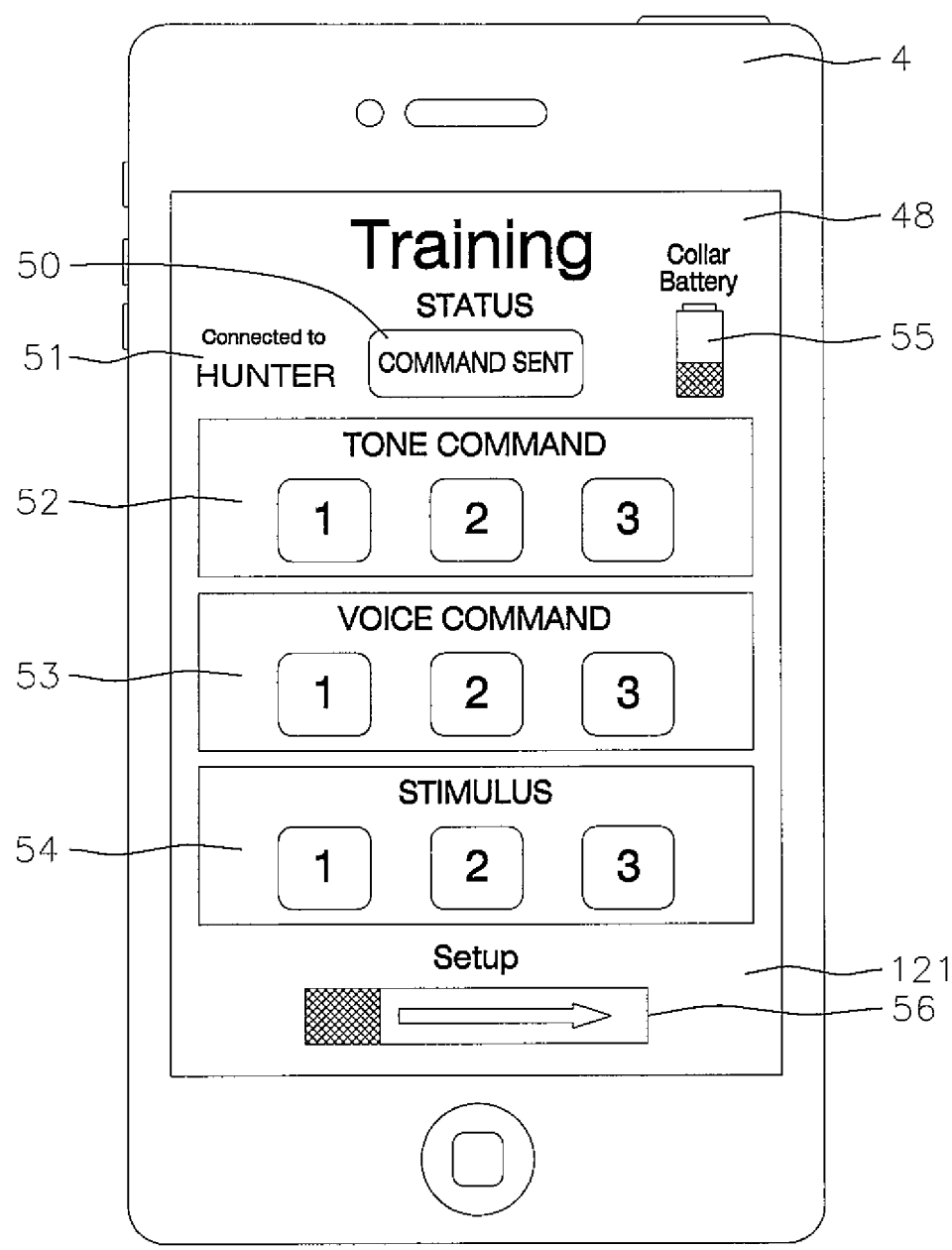
FIG. 12 shows a first training graphical interface that may load when the "Training" application is selected on the wireless mobile device.

FIG. 12 shows a first training graphical interface 121 that may load when the "Training" application is selected on the wireless mobile device 4. The "training" application may be stored in the wireless mobile device's 4 internal memory and, when selected by the human user, may result in the first training graphical interface 121 being displayed on a graphic display panel 48 of the wireless mobile device 4. The first training graphical interface 121 may include a status indicator 50 that indicates the status of the connection between the wireless mobile device 4 and the animal-worn device 1. In one embodiment, a display of "GOOD" indicates that the wireless mobile device 4 is properly paired to the animal-worn device 1 and display of "FAIL" indicates that the two devices are not wirelessly communicating with each other. Other status messages may include "SENT" to indicate when a command is being sent from the wireless mobile device 4 and "ACKNOWLEDGE" to indicate that the command has been received by the animal-worn device 1 and that the animal-worn device 1 has sent back a handshake signal to acknowledge receipt and execution of the command.

The first training graphical interface 121 may include a connected device indicator 51 that displays the name of the animal-worn device 1 with which the wireless mobile device 4 is paired. A tone button array 52 may also be included that includes virtual push buttons to activate unique audible command tones at the animal-worn device 1. Command tones may be discrete single frequency tones much like musical notes or may be more complex pre-programmed audio outputs, examples of which may include the various ring tones available on many commercially available cellular telephones. The use of more complex tones may be more easily identifiable and distinguishable to the animal 4. A voice button array 53 may include virtual push buttons that activate prerecorded voice commands at the animal-worn device 1. The prerecorded voice commands may be recorded at the wireless mobile device 4 and transmitted to the animal-worn device 1 for digital storage in the main processor 18 or the audio recorder 23. They may also be recorded directly into the animal-worn device 1 using the microphone 22. A stimulus button array 54 may be included on the first training graphical interface 121 that includes virtual push buttons that are used to activate electrical stimulus outputs at the electrodes 43 and 44 of the animal-worn device 1 that are generated by the shock generator 33. A battery level indicator 55 may also be included that graphically displays the battery charge level of the animal-worn device 1. Next, a screen slider 56 may be included to switch to additional graphical interfaces in the "Training" application, such as the second training graphical interface 122 shown in FIG. 13.

Figure 13:
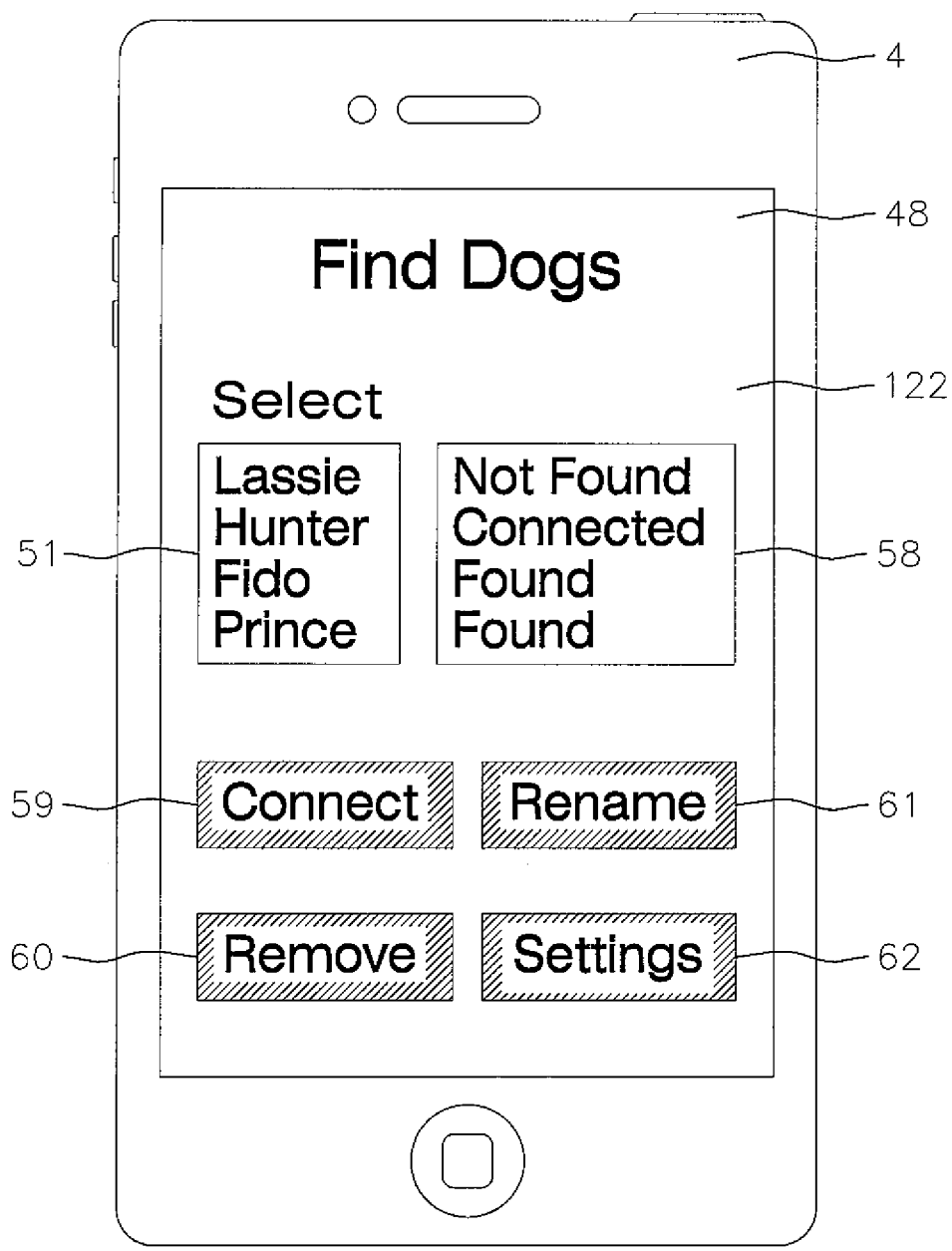
FIG. 13 shows a second training graphical interface being displayed on the graphic display panel of the wireless mobile device as part of the "Training" application.

FIG. 13 shows a second training graphical interface 122 being displayed on the graphic display panel 48 of the wireless mobile device 4. The second training graphical interface 122 may provide information related to the status of animal-worn devices 1 within the detection range of the wireless mobile device 4. In this embodiment, multiple animal-worn devices 1 are displayed, although multiple animal-worn devices 1 are not required. The second training graphical interface 122 may include a stored device list 57 that displays the names of all previously connected animal-worn devices 1 (that have not been removed by the human user). For wireless mobile devices 4 where the graphic display panel 48 is a touchscreen, touching the name of one of the animal-worn devices 1 on the stored device list 57 selects that animal-worn device 1. A remove button 60 may be included on the second training graphical interface 122 to allow the human user to remove the selected animal-worn device 1 from stored device list 57. A rename button 61 may be included to allow the human user to rename the selected animal-worn device 1. Additional features and buttons may be included, such as a "Settings" button 62, which may advance the human user to a third training graphical interface 123 on which setting information for the selected animal-worn device 1 is provided. Although the second training graphical interface 122 is being described as part of the "Training" application, it may also be a part of any other application or subroutine or its own separate application or subroutine.

The second training graphical interface 122 may also include an active status indicator 58 that indicates the wireless status of each animal-worn device 1. A "Not Found" indication on the status indicator 58 may indicate that the animal-worn device 1 is not detected. A "Found" indication may indicate that the animal-worn device 1 is detected but not paired with the wireless mobile device 4. A "Connected" status indication may indicate that the animal-worn device 1 is currently paired with the wireless mobile device. As an alternative to providing the status indicator 58 for all animal-worn devices 1 simultaneously, the second graphic interface may provide only the status indicator 58 for the selected animal-worn device 1.

Figure 14:
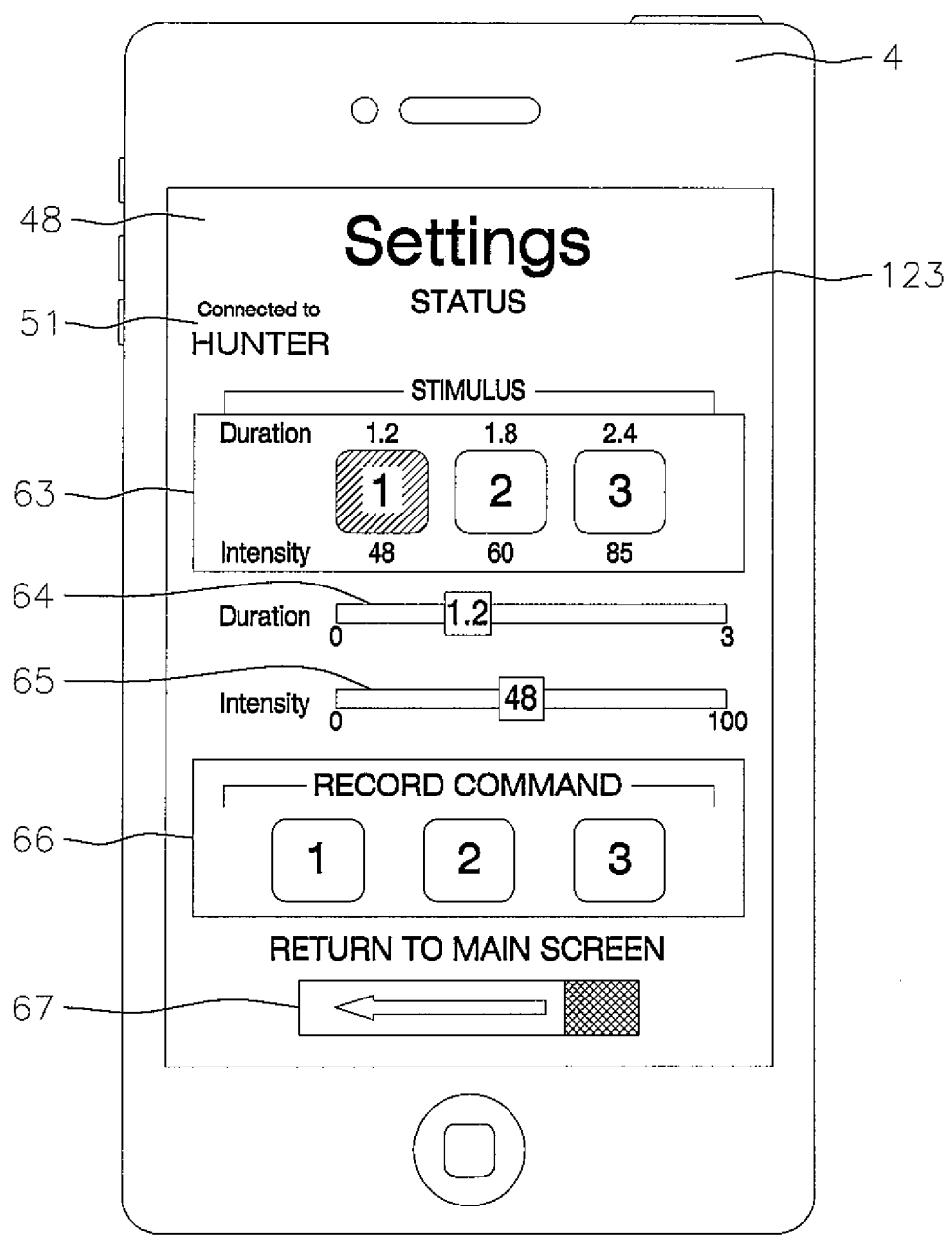
FIG. 14 shows the third training graphical interface being displayed on the graphic display panel of the wireless mobile device as part of the "Training" application.

FIG. 14 shows the third training graphical interface 123 being displayed on the graphic display panel 48 of the wireless mobile device 4. The third training graphical interface 123 may provide "Settings" information regarding the animal-worn device 1 selected on the second training graphical interface 122. The "Settings" graphical interface 123 may include the connected device indicator 51 to indicate the selected animal-worn device 1. "Settings" information may include buttons or the like to allow the human user to set several individually selectable stimulus levels and durations for the selected animal-worn device 1. For example, "Settings" graphical interface 123 may include intensity buttons 63 to allow the human user to select different intensity levels for the shock stimulus sent from the shock generator 33 to the electrodes 43, 44 that are used to correct animal behavior. As an alternative to or in addition to the intensity buttons 63, the "Settings" graphical interface 123 may include an intensity slider 65 that allows the human user to fine tune the level of intensity by sliding a digital dial along the intensity slider 65 to increase or decrease the level of intensity, which may be indicated by the percentage level of the intensity. The "Settings" graphical interface 123 may also include a duration slider 64 to allow the human user to select the length of the shock stimulus sent from the shock generator 33. The "Settings" graphical interface 123 may include "Record Command" options 66 to allow the human user to record commands that can be sent to the animal 3 via the audio processor 35 and speaker 36 so that the human user can provide the animal 3 with a voice command at a later time. For example, this can be used when the animal 3 is at a distance to allow the human user to provide the voice command through the animal-worn device 1. The "Settings" graphical interface 123 may include a return button 67 to allow the human user to return to a previous graphical interface, such as the first training graphical interface 121 or the second training graphical interface 122. Although, in the above embodiments, specific interface features are described as being buttons or sliders, the graphical features described as buttons may be replaced with sliders and vice versa and either may be substituted with any other known graphical interface feature as would be known to a person of ordinary skill in the art.

Figure 15:
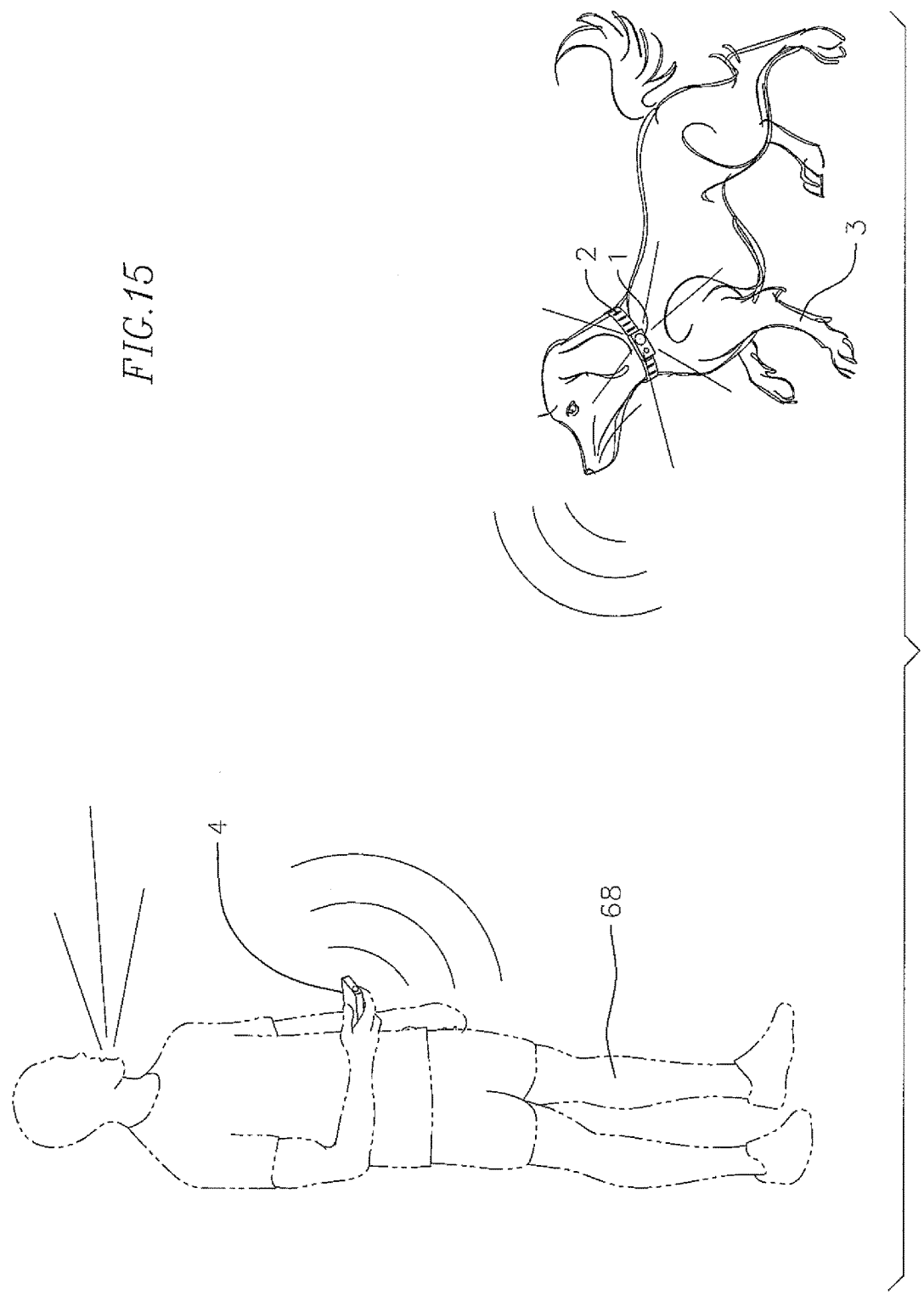
FIG. 15 shows a human user using a speaker to provide a voice command to the animal according to this embodiment of the "Training" application.

FIG. 15 shows the human user 68 using the speaker 36 to provide the voice command to the animal 3 according to this embodiment of the "Training" application. This embodiment allows the human 68 to communicate with the animal 3 via a walkie-talkie type arrangement using the voice receiving ability of the wireless mobile device 4. The "Training" application in the wireless mobile device 4 may allow the human 68 to speak voice commands into the wireless mobile device 4 and then wirelessly transmit the voice commands to the animal-worn device 1 via one of the communication protocols previously described. The animal-worn device 1 may receive the wireless transmission and relay the voice command via the audio processer 35 to the speaker 36. The animal-worn device 1 may then send an acknowledgement back to the wireless mobile device 4 indicating that the incoming signal was received and that the voice command was communicated by the speaker 36.

Figure 16:
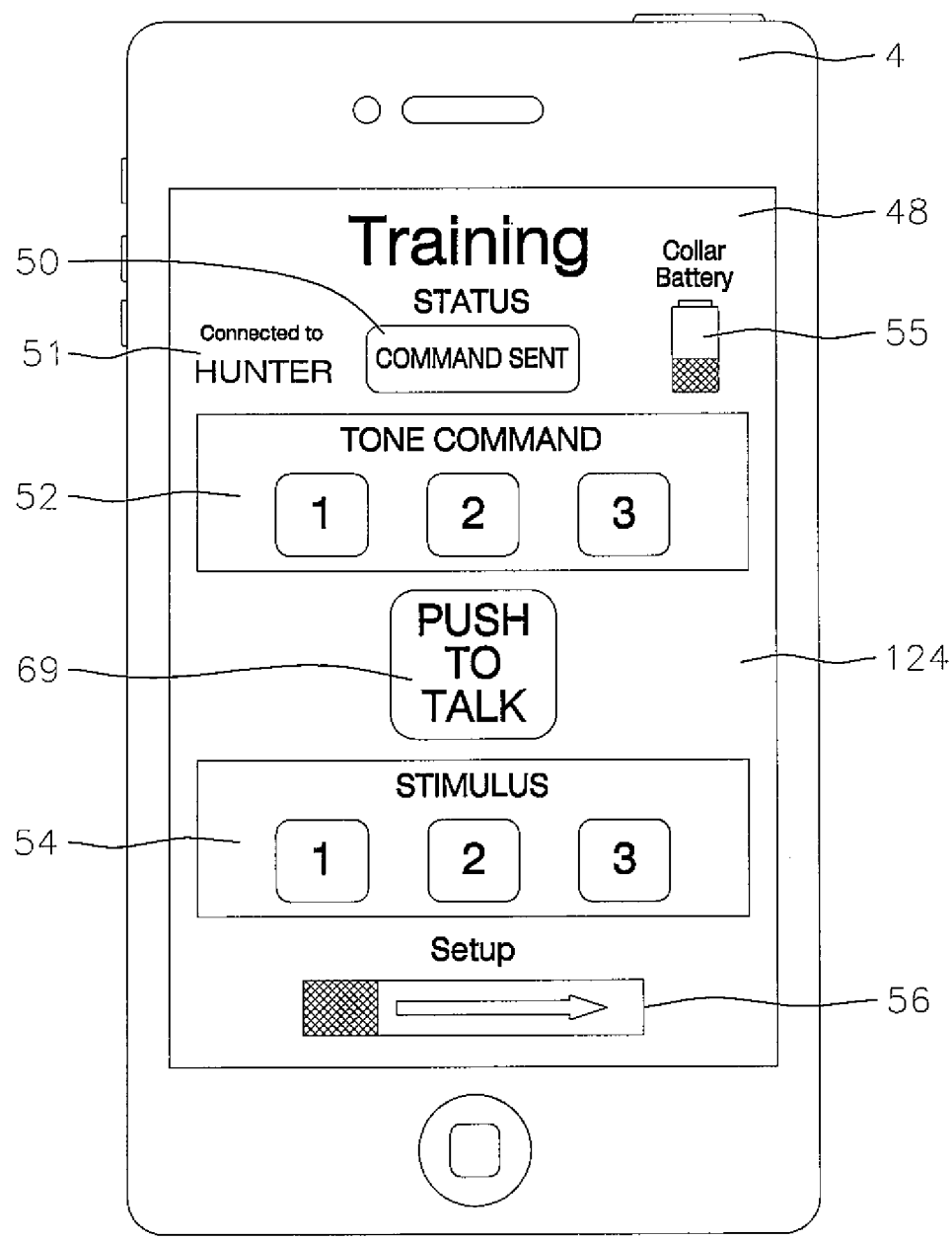
FIG. 16 shows a fourth training graphical interface that may be displayed when the human user is using the "Training" application according to FIG. 15.

FIG. 16 shows a fourth training graphical interface 124 that may be displayed when the human 68 is using the "Training" application described in FIG. 15. The fourth training graphical interface 124 may include the connected device indicator 51 to indicate the selected animal-worn device 1 that will receive the voice commands. The fourth training graphical interface 124 may include the status indicator 50 that indicates the status of the connection between the wireless mobile device 4 and the animal-worn device 1. The status indicator 50 may also indicate if the voice command has been successfully sent and played by the animal-worn device 1. The fourth training graphical interface 124 may also include "Tone Command" options 52 to allow the human 68 to transmit prerecorded tones and/or audio outputs to the animal 3. The prerecorded tones may be, for example, tones imbedded in the "Training" application or tones uploaded or recorded by the human user. The fourth training graphical interface 124 may include "Stimulus" options 54 to allow the human 68 to transmit predetermined stimuli. The levels of the "Stimulus" options 54 may be determined by the human user's selections on the third training graphical interface 123. The fourth training graphical interface 124 may also include a "Push-to-Talk" button 69, which is similar to a walkie-talkie feature, that allows the human 68 to transmit real-time voice commands to the animal 3. "Push-to-Talk" button 69 may be depressed immediately before the voice command is enunciated. Once spoken, the voice command is sent to the animal-worn device 1. The fourth training graphical interface 124 may include the next screen slider 56 to switch to additional graphical interfaces in the "Training" application. The battery level indicator 55 may also be included that graphically displays the battery charge level of the animal-worn device 1.

Figure 17:
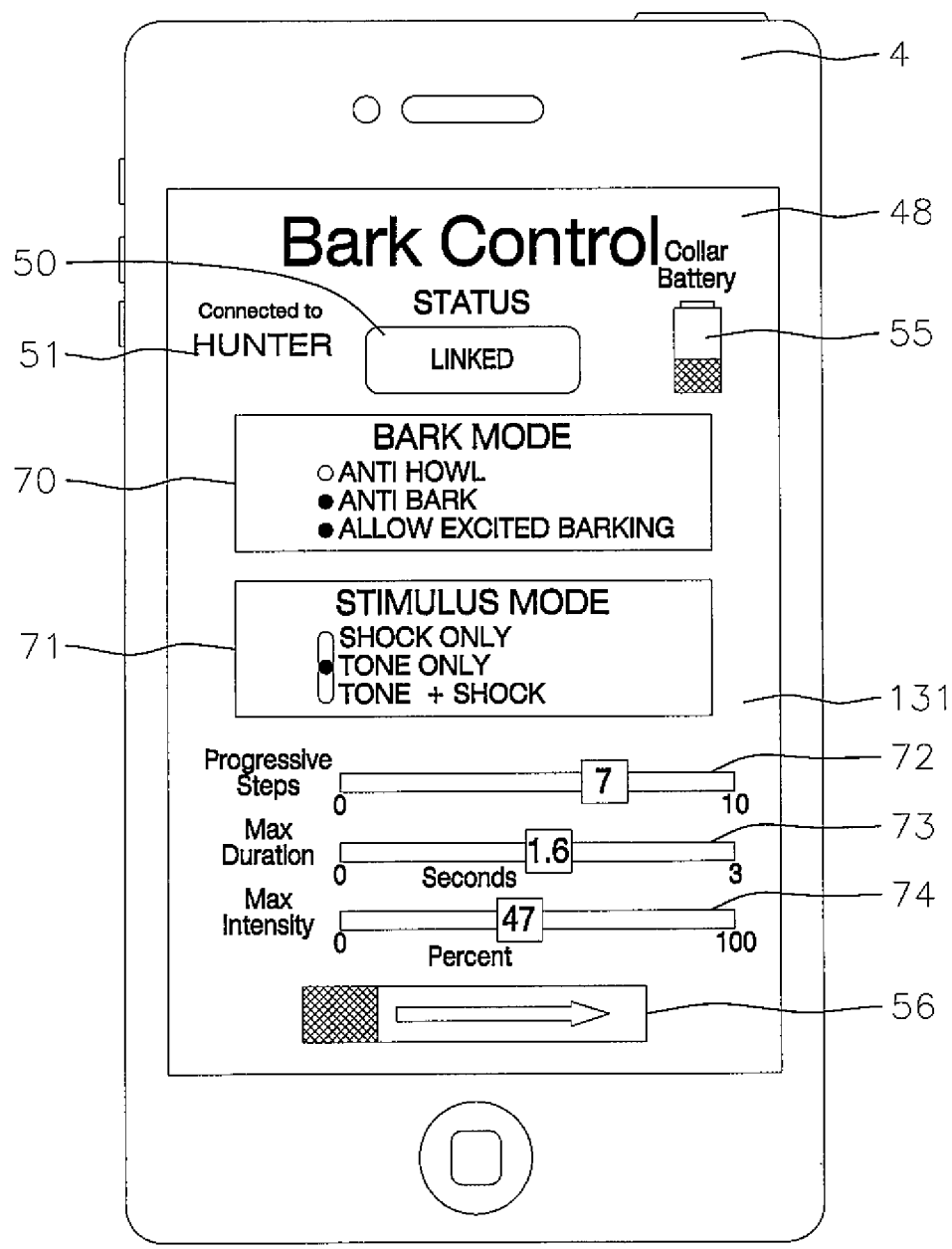
FIG. 17 shows a first bark control graphical interface being displayed on the graphic display panel of the wireless mobile device that may load when the "Bark Control" application is selected on the wireless mobile device.
Figure 18:
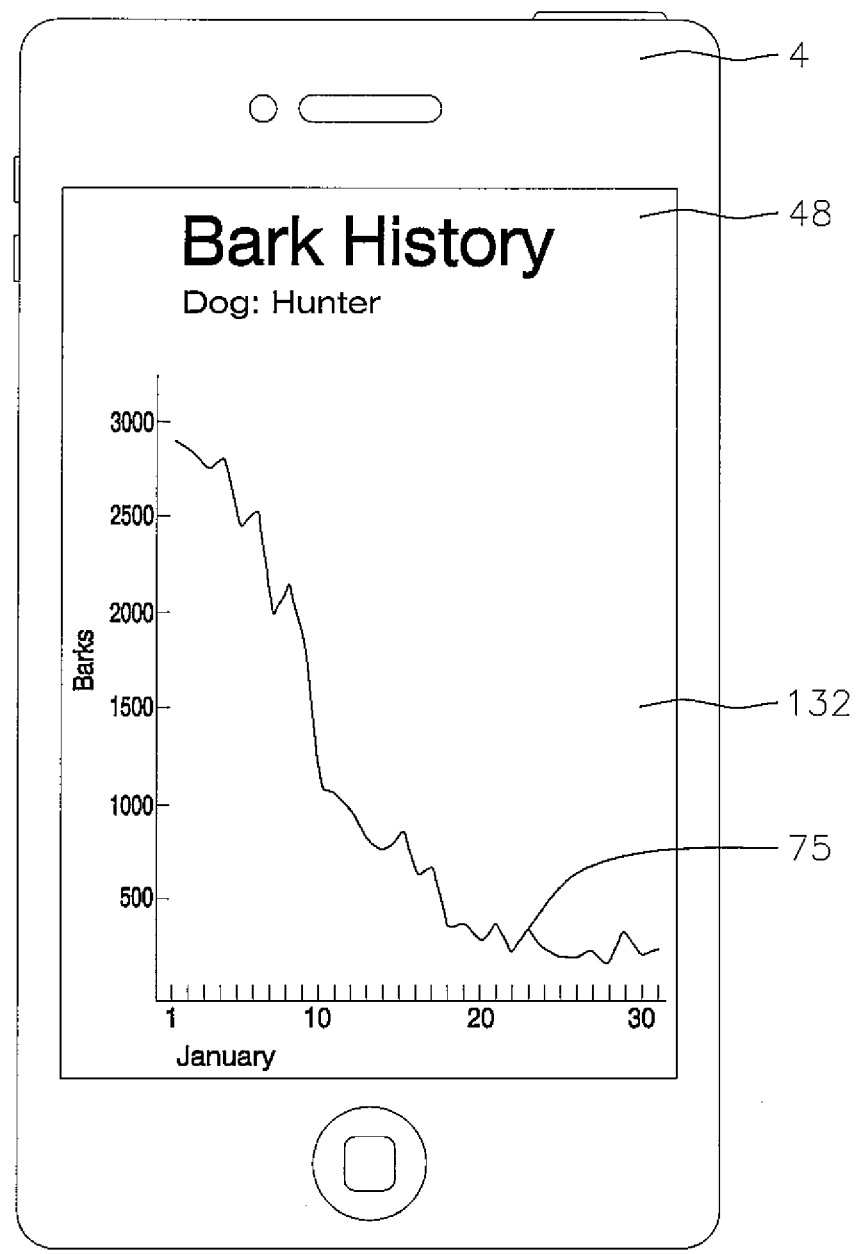
FIG. 18 shows a second bark control graphical interface that may be displayed on the graphic display panel of the wireless mobile device as part of the "Bark Control" application.

FIGS. 17-18 show graphical interfaces and a representational diagram of an embodiment of a "Bark Control" application. The "Bark Control" application may be used to train the animal 3 to refrain from certain types of unwanted barking and/or growling while allowing others.

FIG. 17 shows a first bark control graphical interface 131 being displayed on the graphic display panel 48 of the wireless mobile device 4 that may load when the "Bark Control" application is selected on the wireless mobile device 4. The first bark control graphical interface 131 may be for controlling different types of barking by selecting the bark to be controlled and selecting the type of stimulus to be used to control that type of barking. A bark mode selector 70 may be included that allows the human user to select the type of barks that are to be controlled. For example, the human user may select an option on the bark mode selector 70 that focuses on controlling howling (e.g., "Anti-Howl") or that focuses on controlling barking in general (e.g., "Anti-Bark"). The bark mode selector 70 may also include options to allow specific types of barking without receiving a stimulus (e.g., "Allow Excited Barking"). A stimulus mode selector 71 may be included that allows the human user to select the type of stimulus to be generated in response to the selected type of bark. For example, the human user may be able to select options such as "Shock Only," "Tone Only" or "Tone and Shock" and other possible stimuli that can be selected to occur when the selected barking occurs. The first bark control graphical interface 131 may also include different buttons or sliders to control the level and intensity of a stimulus. For example, the interface 131 may include a progressive step slider 72, a maximum duration slider 73, and/or a maximum intensity slider 74 to control characteristics of a shock stimulus. The progressive step slider 72 may allow the human user to control the rate of increase in the level of the shock stimulus that occurs if the animal 3 continues to utter the selected bark. The maximum duration slider 73 may allow the human user to control the maximum length of time for which the shock stimulus persists. The maximum intensity slider 74 may allow the human user to control the maximum level of intensity of the shock stimulus that is given to the animal 3. These sliders or other sliders, buttons or the like may be included that allow the human user to control the characteristics of the stimulus or stimuli to be given to the animal 3.

The first bark control graphical interface 131 may also include the connected device indicator 51 to indicate the animal-worn device 1 that has been selected, such as via the second training graphical interface 122 or similar graphical interface included in the "Bark Control" application. It may also include the status indicator 50 that indicates the status of the connection between the wireless mobile device 4 and the animal-worn device 1. The battery level indicator 55 may also be included that graphically displays the battery charge level of the animal-worn device 1. The first bark control graphical interface 131 may include the next screen slider 56 to switch to additional graphical interfaces in the "Bark Control" application.

FIG. 18 shows a second bark control graphical interface 132 that may be displayed on the graphic display panel 48 of the wireless mobile device 4. The second bark control graphical interface 132 displays one embodiment of a graphical representation of the bark history of the animal 3.

Similar graphical representations including charts, tables or the like may be included in the "Bark Control" application to show the progress of the animal 3 over the course of the bark control training. In this embodiment, the second bark control graphical interface 132 shows a line graph 75 representing the number of barks by the animal 3 that have occurred on a daily basis throughout the month of January. Other similar graphs may be included, such as representing the number of barks over a different period of time, such as hourly, monthly or annually, or representing specific types of bark over time, or comparing different types of barks by the animal 3. The "Bark Control" application may also be able to send alerts, such as via email, SMS, website postings (e.g., Facebook, Twitter, etc.) or instant messaging, alerting the user that the animal is barking. These alerts may include information regarding the type of barking, such as whether the barking is excited, excessive or whether the animal is howling.

Figure 19:
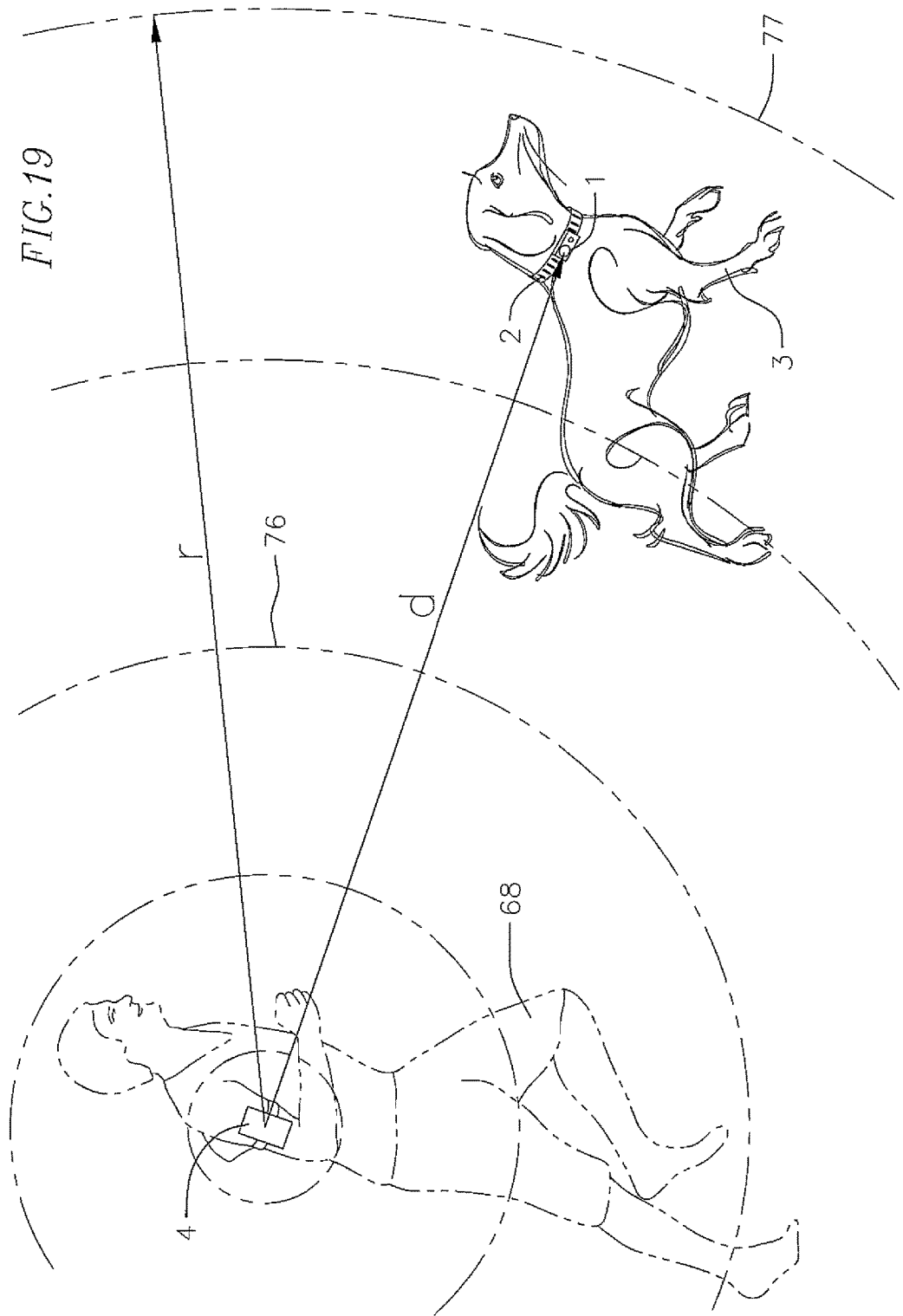
FIG. 19 shows an example of the human using the "Leash Control" application to tether the animal.
Figure 20:
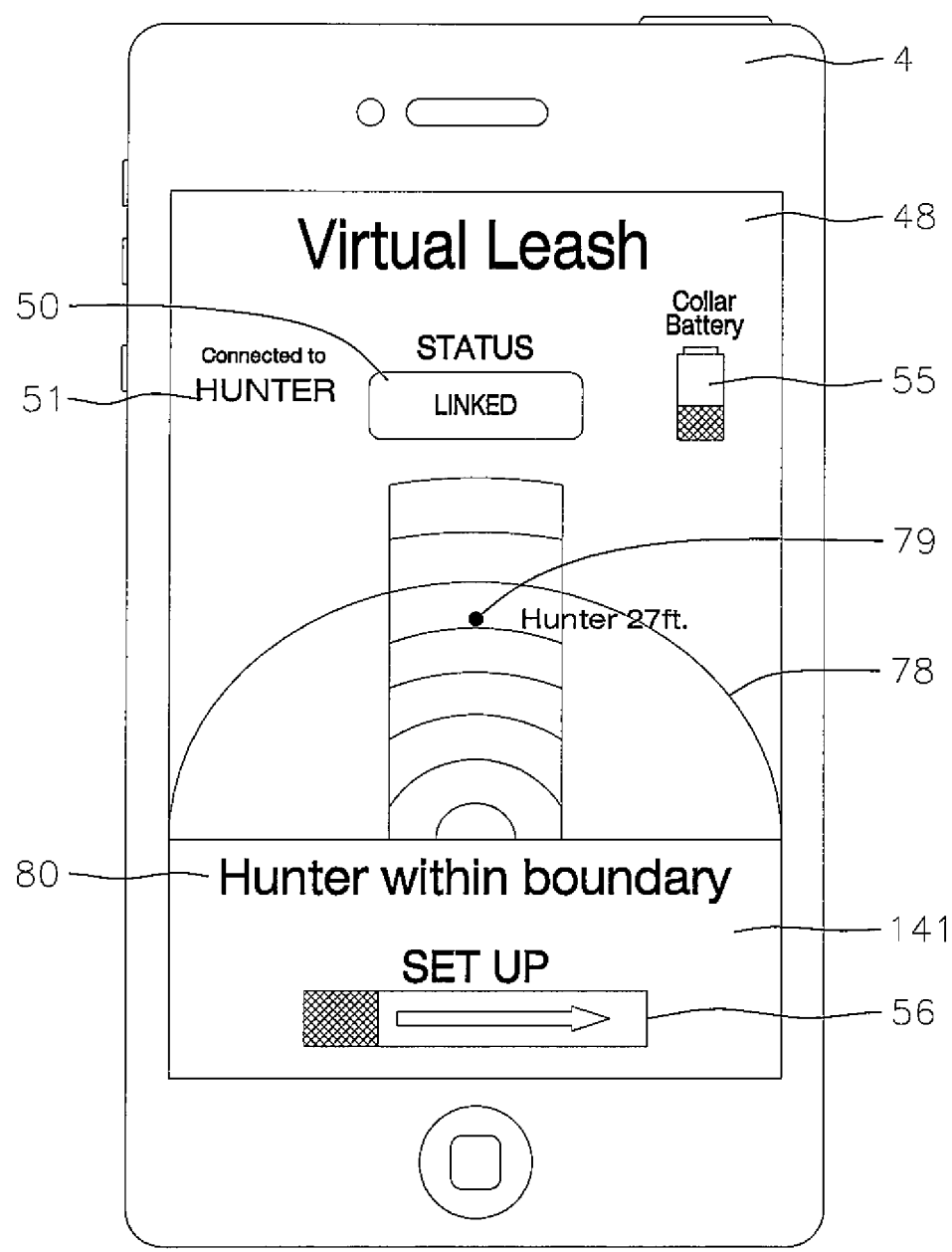
FIG. 20 shows a first leash control graphical interface being displayed on the graphic display panel of the wireless mobile device that may load when the "Leash Control" application is selected on the wireless mobile device.
Figure 21:
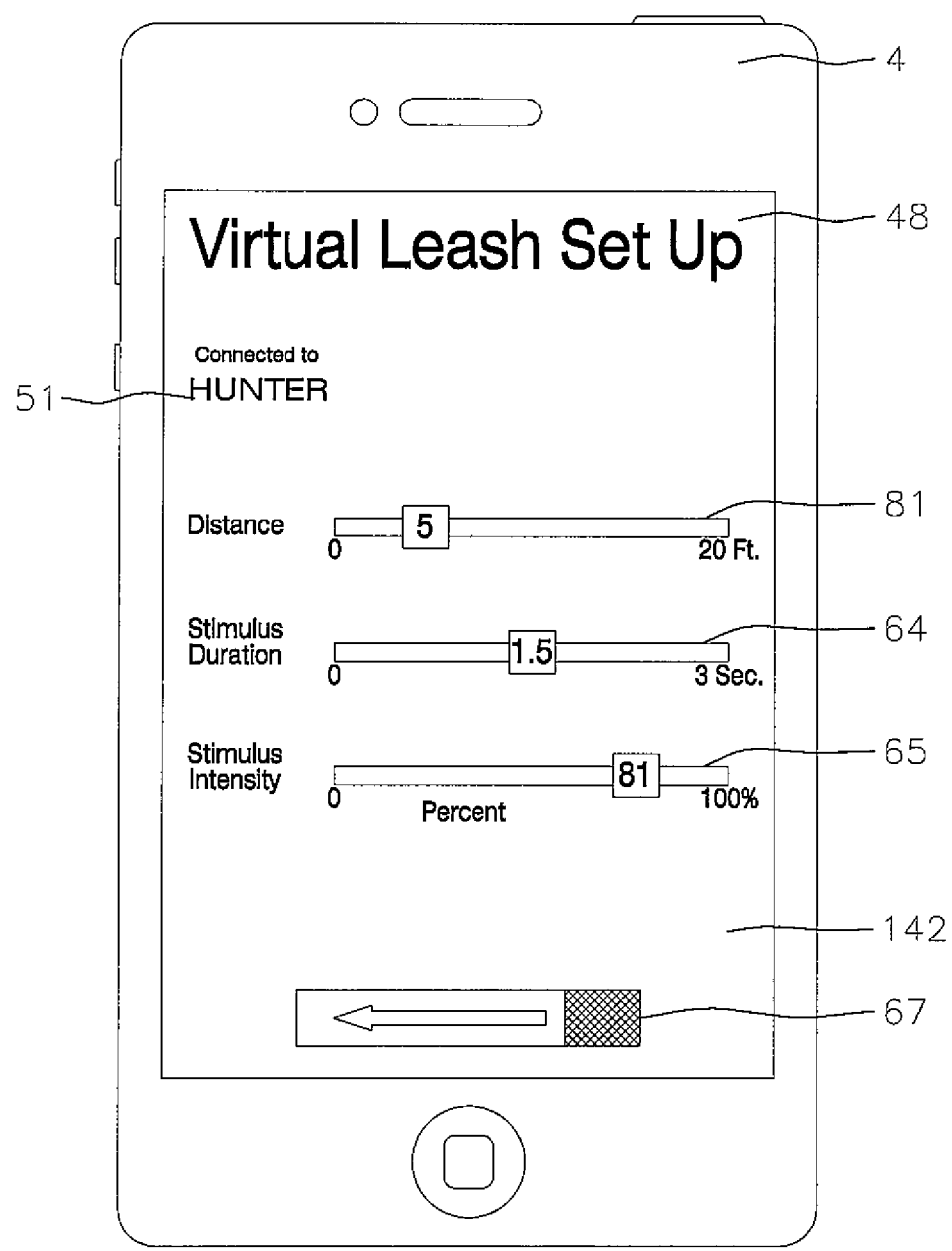
FIG. 21 shows a second leash control graphical interface that may be displayed on the graphic display panel of the wireless mobile device as part of the "Leash Control" application.

FIGS. 19-21 show graphical interfaces and representational diagrams of an embodiment of a "Leash Control" application. Using RSSI or other ranging techniques, the "Leash Control" application may alert the human user 68 when the animal 3 has strayed beyond a predetermined range of separation between the wireless mobile device 4 and the animal-worn device 1. Stimulus may be applied to the animal via outputs at the animal-worn device 1 to encourage the animal 3 to return to a position within the predetermined range. This may be especially useful when the human 68 is physically training with the animal 3, for example, when the human 68 and the animal 3 are running side by side or the animal 3 is running alongside the human 68 who is riding a bicycle. This "Leash" application along with the animal-worn device 1 avoids the need for a physical leash.

FIG. 19 shows an example of the human 68 using the "Leash Control" application to tether the animal 3 while jogging. In this embodiment, the wireless mobile device 4 can emit a radio signal 76 and the "Leash Control" application uses the RSSI of the emitted radio signal 76 to determine a distance d of the wireless mobile device 4 from the animal-worn device 1. Although in this embodiment the wireless mobile device 4 is emitting the radio signal 76, an auxiliary transmitting device may also be used to emit the radio signal 76. Using the RSSI, the "Leash Control" application allows human user to select a predetermined boundary 77 and if the animal-worn device 1 moves farther from the wireless mobile device 4 than the predetermined boundary 77, specific outputs can be triggered or deactivated. For example, if the animal-worn device 1 moves outside the predetermined boundary 77, the animal-worn device 1 may send a stimulus to the animal 3, such as a shock stimulus via the electrodes 43, 44. The radio signal 76 used to create the predetermined boundary 77 may use the same frequency as for data transmission or the boundary signal may be transmitted separately using a frequency conducive to the particular RSSI decoding technique employed. Although this embodiment is in effect while the human 68 is jogging, the "Leash Control" application may also be used when the human 68 is performing any of a variety of activities, including walking, hiking or biking.

FIG. 20 shows a first leash control graphical interface 141 that may be displayed on the graphic display panel 48 of the wireless mobile device 4. The first leash control graphical interface 141 may provide information regarding the relative position of the animal 3 to the predetermined boundary 77. For example, the first leash control graphical interface 141 may provide a pictorial representation of the animal 3 relative to the predetermined boundary 77 via a graphical representation of the predetermined boundary 77, in this example represented by the line 78, and a graphical representation of the animal-worn device 1, in this example represented by the dot 79. Although a line and a dot are used in this example, other symbols or shapes may be used, including, for example, a small animal cartoon to represent the animal 3. The first leash control graphical interface 141 may also include a boundary status indicator 80 to indicate whether the animal 3 is within or outside of the predetermined boundary 77, such as by using different colored textual statements.

The first leash control graphical interface 141 may include the status indicator 50 that indicates the status of the connection between the wireless mobile device 4 and the animal-worn device 1. The first leash control graphical interface 141 may include the connected device indicator 51 to indicate the animal-worn device 1 that has been selected, such as via the second training graphical interface 122 or similar graphical interface included in the "Leash Control" application. The battery level indicator 55 may also be included that graphically displays the battery charge level of the animal-worn device 1. The screen slider 56 may be included to switch to additional graphical interfaces in the "Leash Control" application.

FIG. 21 shows a second leash control graphical interface 142 that may be displayed on the graphic display panel 48 of the wireless mobile device 4. The second leash control graphical interface 142 may include setup information to allow the human user to configure the settings of the "Virtual Leash" application. A distance slider 81 may be included to allow the human user to select the distance from the wireless mobile device 4 where the predetermined boundary 77 will exist. The duration slider 64 may be included to allow the human user to select the length of the shock stimulus or other stimulus sent from the shock generator 33, the tone generator 37, etc. The intensity slider 65 may be included to allow the human user to fine tune the level of intensity by sliding the digital dial along the intensity slider 65 to increase or decrease the level of intensity, which may be indicated by the percentage level of the intensity. The second leash control graphical interface 142 may also include the connected device indicator 51 to indicate the animal-worn device 1 that has been selected. The second leash control graphical interface 142 may include the return button 67 to allow the human user to return to a previous graphical interface, such as the first leash control graphical interface 141.

Figure 22:
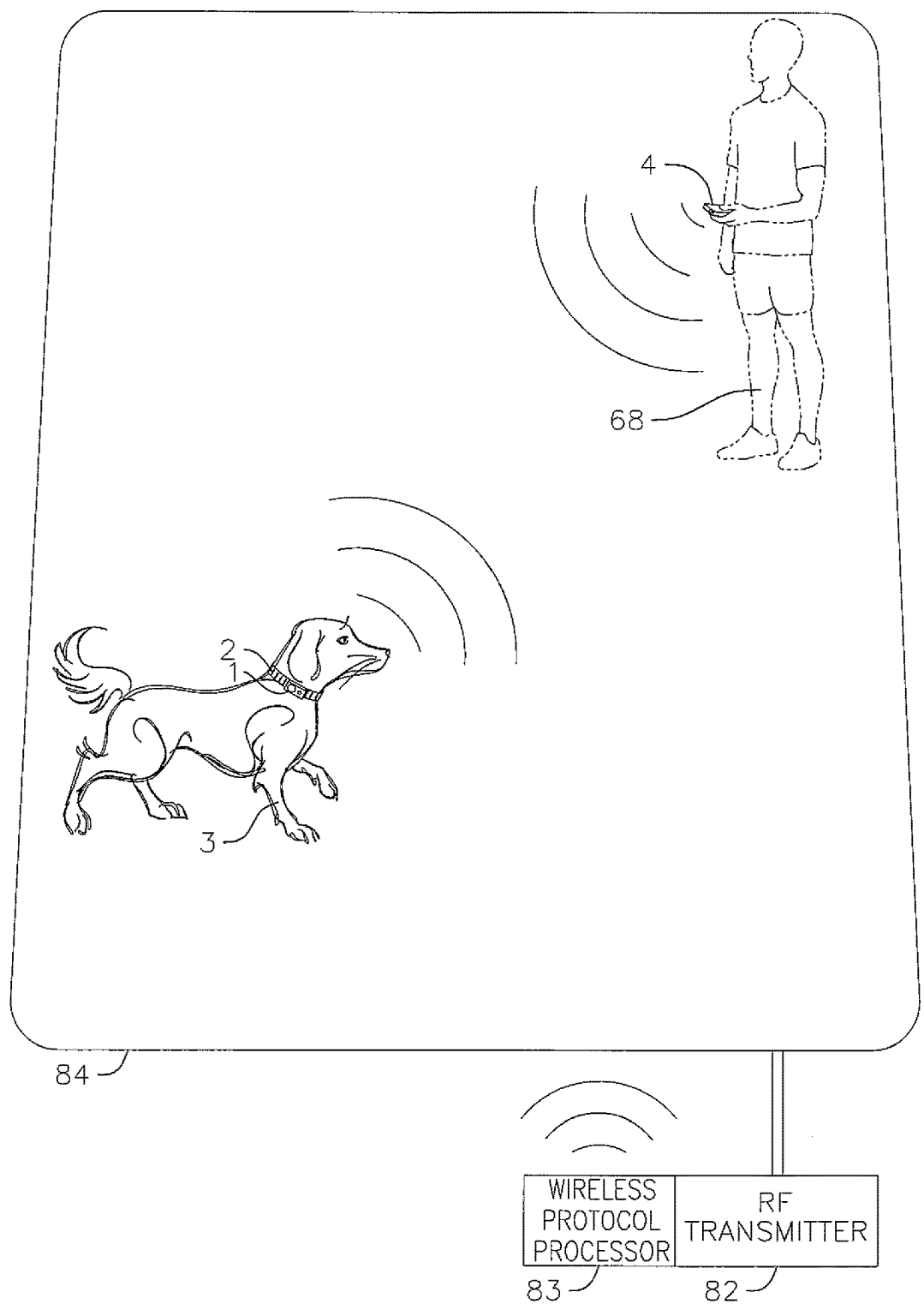
FIG. 22 is a representational diagram of an animal containment system that may be controlled by an "Electronic Fence" application on the wireless mobile device 4.

FIG. 22 is a representational diagram of an animal containment system that may be controlled by an "Electronic Fence" application on the wireless mobile device 4. This embodiment uses a wire perimeter antenna 84 that may emit, a low, frequency radio field around the wire perimeter antenna 84 based on inputs from an RF transmitter 82. The RE transmitter 82 may be controlled by the wireless mobile device 4 via a wireless protocol transceiver 83 that communicates with the wireless mobile device 4. The wireless mobile device 4 may communicate with the wireless protocol transceiver 83 through any of the communication protocols discussed above, including BLUETOOTH and WiFi. Through the "Electronic Fence" application on the wireless mobile device 4, the human user 68 may instruct the animal-worn device 1 to activate a stimulus, such as a shock or tone output, whenever the animal 3 comes within the radio field of the perimeter antenna 84. The human user 68 may also be able to instruct the animal worn device to activate different stimuli based on the proximity of the animal 3 to the wire perimeter antenna 84 within the radio field. The "Electronic Fence" application may be capable of activating the RF transmitter 82, controlling the width of the radio field emitted by the wire perimeter antenna 84, and/or controlling the intensity, duration and other attributes of the stimulus to be given to the animal when it comes within the radio field of the perimeter antenna 84. The "Electronic Fence" application may also store information regarding the number of times the animal 3 breached the radio field of the perimeter antenna 84 and display that information to the human user 68 on the wireless mobile device 4. The "Electronic Fence" application may also be able to send alerts, such as via email, SMS, website postings or instant messaging, alerting the user that the animal has breached the fence perimeter.

Figure 23:
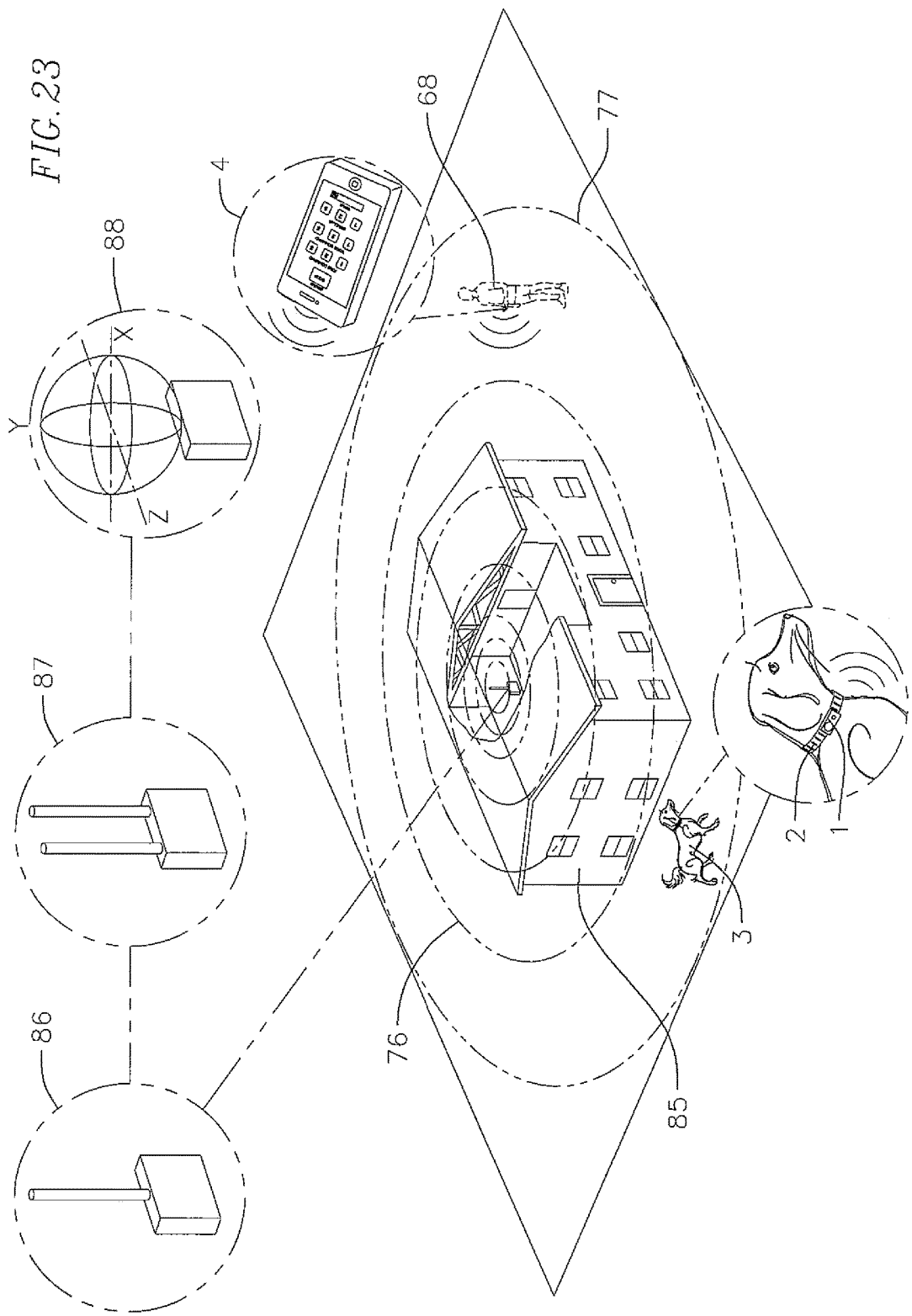
FIG. 23 is a representational diagram of an animal containment system that may be controlled by a "Wireless Fence" application on the wireless mobile device 4.

FIG. 23 is a representational diagram of an animal containment system that may be controlled by a "Wireless Fence" application on the wireless mobile device 4. A wireless fence transmitter 86, 87, or 88 may emit a radio signal 76 and the "Wireless Fence" application uses the RSSI of the emitted radio signal 76 to determine a distance of the wireless mobile device 4 from the animal-worn device 1. Using the RSSI, the "Wireless Fence" application allows the human user to select a predetermined boundary 77 and if the animal-worn device 1 moves farther from the wireless mobile device 4 than the predetermined boundary 77, specific outputs can be triggered or deactivated. For example, if the animal-worn device 1 moves outside the predetermined boundary 77, the animal-worn device 1 may send a stimulus to the animal 3, such as a shock stimulus via the electrodes 43, 44. Time of flight and other wireless localizing techniques may be employed to locate the animal-worn device 1 relative to the wireless fence transmitter 86, 87, or 88 and send the location data to the wireless mobile device 4. In the current embodiment, the wireless fence transmitter 86, 87, or 88 is installed at a house 85, however, the wireless fence transmitter 86, 87, or 88 may be installed at any area where containment of the animal 3 is desired.

FIG. 23 provides three alternative wireless fence transmitters that, may emit the radio signal 76: a single antenna wireless fence transmitter 86, a dual antenna wireless fence transmitter 87 or a radial loop wireless fence transmitter 88. The single antenna wireless fence transmitter 86 has a single antenna and may emit the same type of radio signal as is used by the wireless mobile device 4. For example, the single antenna wireless fence transmitter 86 may emit a BLUETOOTH or WiFi signal as the radio signal 76. In addition, the single antenna wireless fence transmitter 86 may have RSSI built into the transmitter. Using the same radio signal for containment and communication provides numerous advantages including reducing the number of system components.

The dual antenna wireless fence transmitter 87 has two antennae and may emit the same type of radio signal as is used by the wireless mobile device 4. For example, the dual antenna wireless fence transmitter 87 may emit a BLUETOOTH or WiFi signal as the radio signal 76. In addition, the dual antenna wireless fence transmitter 87 may have RSSI build into the transmitter. The two antennae of the dual antenna wireless fence transmitter 87 are spaced by at least half a wavelength, which can help increase the consistency of the containment system by preventing the occurrence of nodes which could create localized "holes" in the wireless fence. In a particular embodiment, the use of two antennae also allows for a reduction of the multipath effect. Multipath refers to the fact, that a reflected signal will have a longer path getting from a transmitter to a receiver than would a direct signal. Depending on the frequency and the geometry of the situation, the two signals may be in phase and additive, producing a high RSSI, or may be out of phase and subtractive producing a low RSSI, or may be any phase between the two. For a given geometry there will be a frequency which is additive, and other frequency which is subtractive. The difference in these two frequencies becomes less as the distance of the direct signal becomes greater. In one particular communication protocol, BLUETOOTH BLE, frequency hops over a large enough range of frequencies that at least one additive and one subtractive channel are usually available for any geometry with a direct path distance longer than 50 feet. At shorter distances where signal strength is very high, accurate RSSI is not needed because the pet is well within the containment boundary.

The multipath effect of direct and reflected RF signals makes it difficult to estimate distance between a transmitter and receiver using just the magnitude of RSSI at the receiver. This, is especially true in the 2.4 GHz frequency band where a wavelength is only about 5 inches. However, using multiple antennae in addition to, in one embodiment, taking advantage of the frequency hopping property of BLUETOOTH Low Energy 4.0 communications at 2.4 GHz, helps to mitigate the phase cancellation effect by keeping a history of the reported signal strength for each band compared to the average of all bands, and predicting for each band the ratio of its signal strength versus the average. This allows the animal-worn transmitter 1 to operate as an RF containment system, by sensing the approximate distance from a central BLUETOOTH transmitter, such as the dual antenna wireless fence transmitter 87. If the distance is too great, the collar may produce various stimuli which instruct the pet to return to an acceptable distance, thus implementing a containment system with a circular invisible fence centered at the BLUETOOTH transmitter.

The radial loop wireless fence transmitter 88 is a known type of transmitter in the field including three loop antennas each on a different axis. The radial loop wireless fence transmitter 88 uses a low frequency signal that may be lower than 100 kHz, or even lower than 20 kHz. With such low frequencies, the radio signal 76 emitted by the radial loop wireless fence transmitter 88 can penetrate through most objects, such as the house 85. In addition, using three loop antennae can increase the signal strength by summing the signal strengths along the three axes.

In a further embodiment, the radio signal 76 of any of the above described containment systems may act as a beacon to activate a GPS locator 26 in the animal-worn device 1 when the signal strength of the radio signal 76 decreases below a predetermined threshold.

Figure 24:
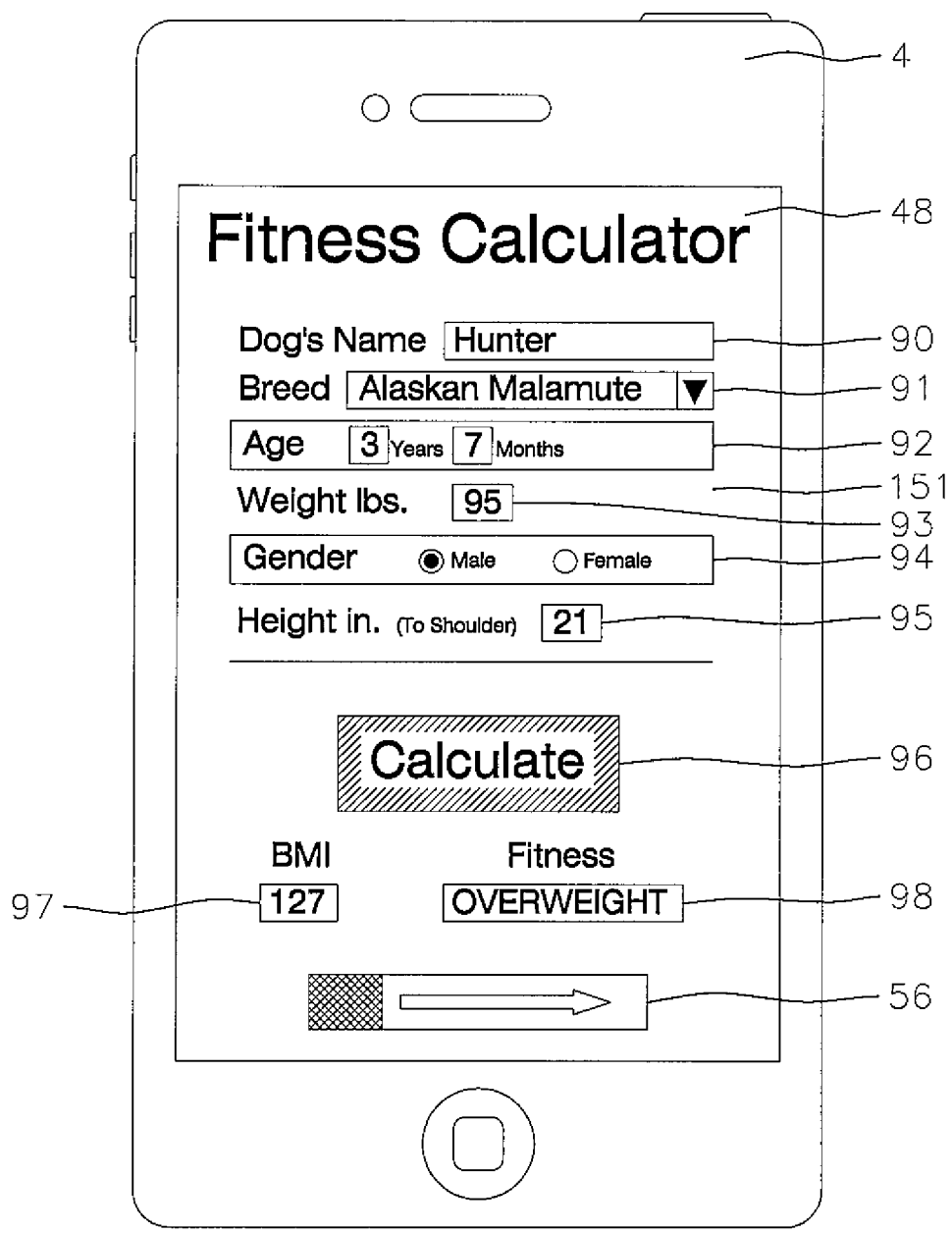
FIG. 24 shows a first fitness graphical interface being displayed on the graphic display panel of the wireless mobile device that may load when the "Fitness" application is selected on the wireless mobile device.
Figure 25:
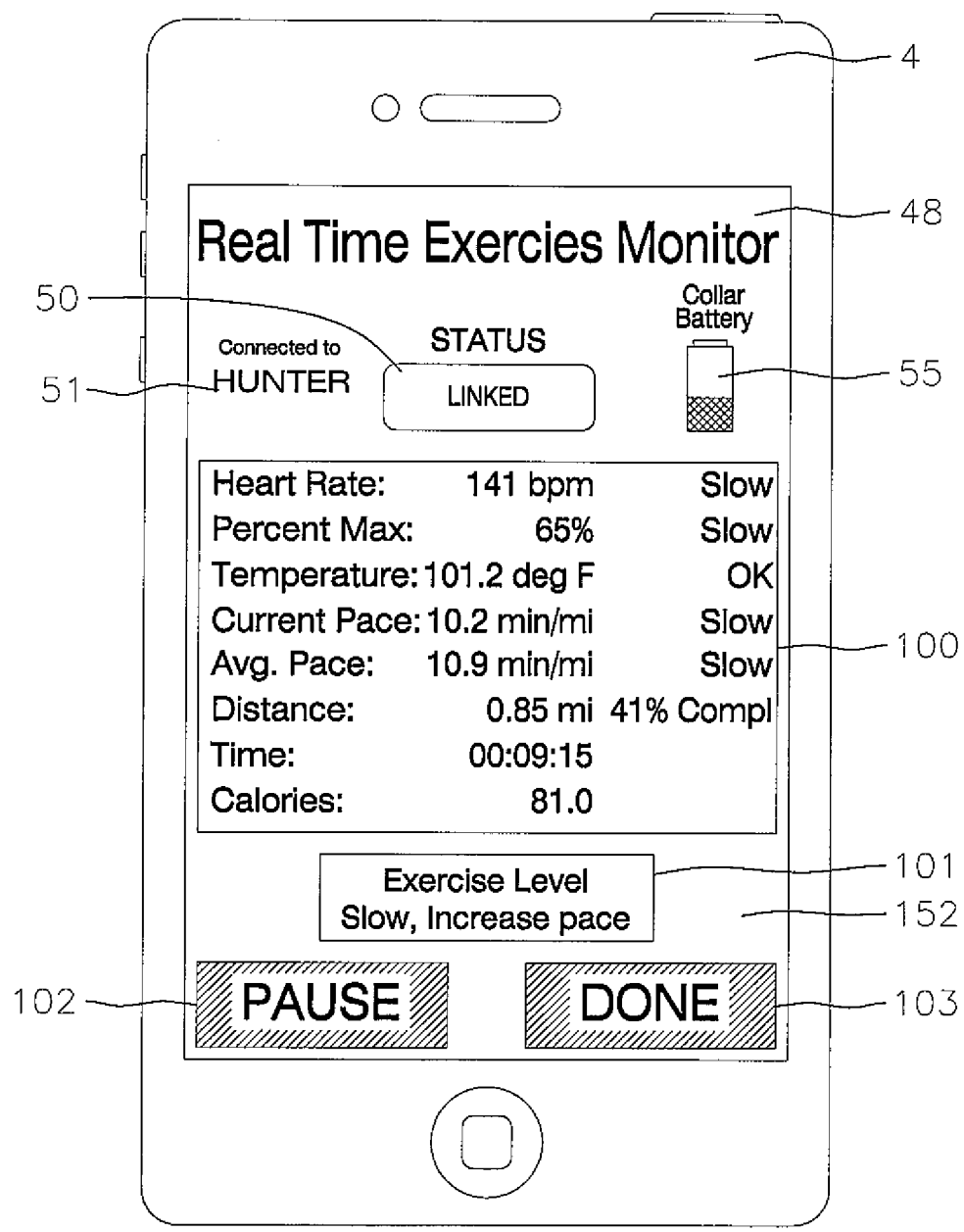
FIG. 25 shows a second fitness graphical interface being displayed on the graphic display panel of the wireless mobile device as part of the "Fitness" application.
Figure 26:
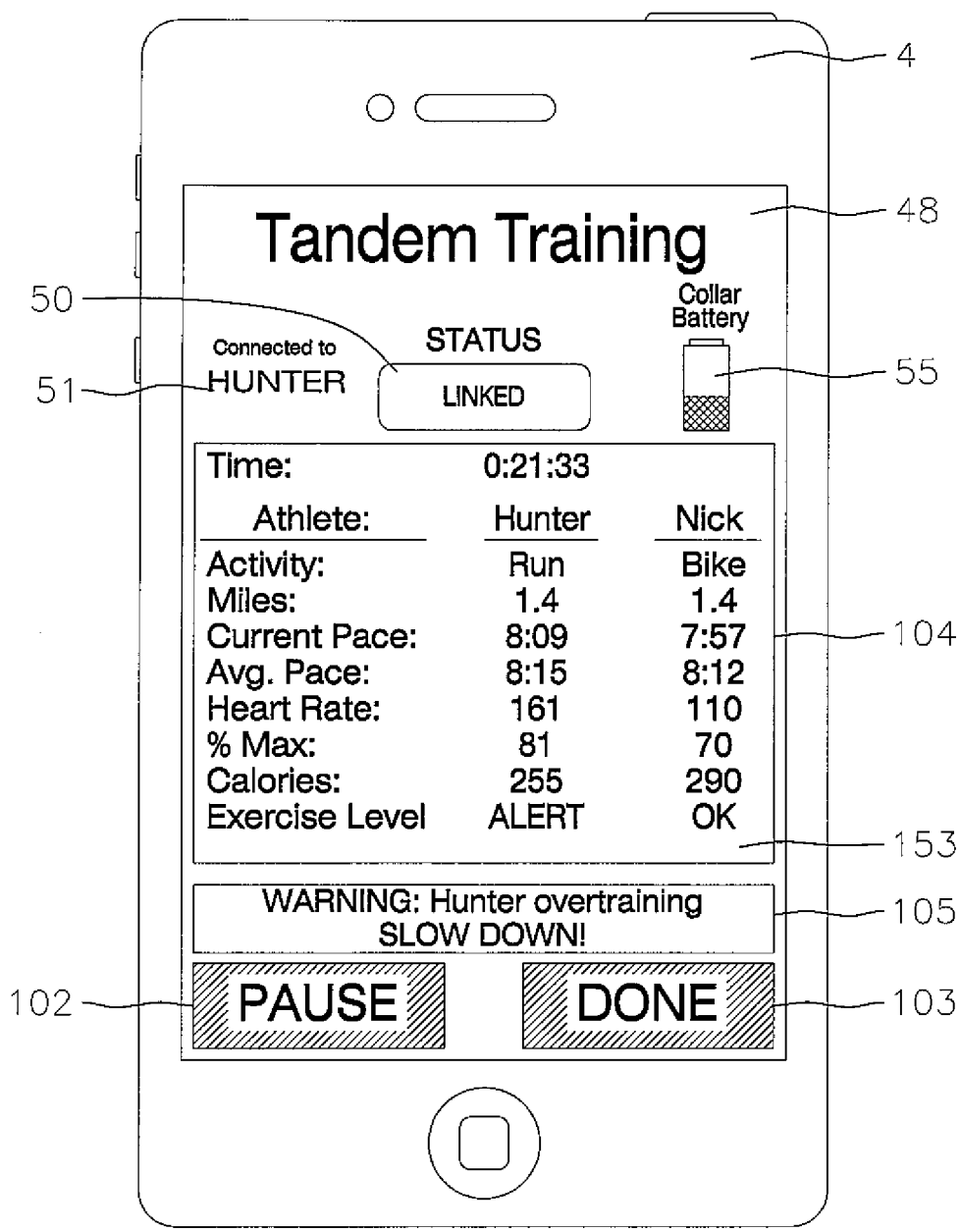
FIG. 26 shows a third fitness graphical interface being displayed on the graphic display panel of the wireless mobile device as part of the "Fitness" application.

FIGS. 24-26 show graphical interfaces and a representational diagram of an embodiment of a "Fitness" application. The "Fitness" application may allow the human 68 to conduct exercise sessions with the animal 3 wearing the animal-worn device 1 and to observe the fitness and vital signs of the animal as the session progresses. Software in the wireless mobile device 4 may analyze data generated at the animal-worn device 1 and advise the human when the training level needs adjustment in order to maintain a desired heart rate, calorie burn or other benchmark fitness criteria. The "Fitness" application may also allow the human user to physically train along with the animal and display data pertaining to the exercise level of both the animal 3 and the human 68.

FIG. 24 shows a first fitness graphical interface 151 being displayed on the graphic display panel 48 of the wireless mobile device 4 that may load when the "Fitness" application is selected on the wireless mobile device 4. The first fitness graphical interface 151 may provide a fitness calculator to estimate the overall body mass index (BMI) of the animal 3 based on information input by the human user. The first fitness graphical interface 151 may include a name input field 90 where the human user may input the name of the animal 3. A breed input field 91 may be included where the human user may choose the breed of the animal from a pull-down list. An age input field 92 may be included where the human user may input the age of the animal 3. A weight input field 93 may be included where the human user may input the weight of the animal 3. A gender selection field 94 may be included where the human user may select the gender of the animal 3. A height input field 95 may be included where the human user may input the height of the animal 3. The first fitness graphical interface 151 may include a "Calculate" button that when pressed after the human user has input the above information, will initiate instructions stored in the "Fitness" application to calculate the EMI of the animal 3 and display the calculated BMI on the BMI display 97. The instruction stored in the "Fitness" application may calculate BMI based on all or some of the information input by the human user. Additional input fields may be included in order to more precisely calculate the BMI of the animal 3. The first fitness graphical interface 151 may also include a fitness level display 98, which provides a general statement of the animal's fitness based on the BMI or other input information. The fitness level display 98 may include statements such as "Overweight," "Healthy," or "Underweight" as a general assessment of the animal's overall health. The first fitness graphical interface 151 may include the screen slider 56 that allows the human user to switch to additional graphical interfaces in the "Fitness" application.

FIG. 25 shows a second fitness graphical interface 152 being displayed on the graphic display panel 48 of the wireless mobile device 4. The second fitness graphical interface 152 may monitor exercise information regarding the animal 3 in real-time when the animal 3 is performing an exercise routine. It may provide buttons such as a start/pause button 102 to allow the human user to begin or pause the exercise routine. It may also include a "done" button 103 that ends the exercise routine. During the animal's 3 exercise routine, the second fitness graphical interface 152 may provide statistics regarding the animal's 3 performance in an exercise data array 100. The exercise data array 100 may include statistics of the exercise routine, such as the animal's 3 heart rate, percentage of heart rate relative to maximum heart rate, internal temperature, current pace, average pace, distance traveled, time elapsed and calories burned. The second fitness graphical interface 152 may also include an exercise level indicator 101 that displays recommendations as to whether the animal's 3 exercise level should be increased or decreased based on some or all the statistics in the exercise data array 100 and/or the input fields from the first fitness graphical interface 151 and outputs a recommendation to advise the human 68 as to when the training level needs adjustment in order to maintain a desired heart rate, calorie burn or other benchmark fitness criteria. For example, recommendations may be determined by comparing target training levels, which may be based on information input on the first graphical interface 151, to the animal's real-time activity level.

The second fitness graphical interface 152 may also include the connected device indicator 51 to indicate the animal-worn device 1 that has been selected. It may include the status indicator 50 that indicates the status of the connection between the wireless mobile device 4 and the animal-worn device 1. It may also include the battery level indicator 55 that graphically displays the battery charge level of the animal-worn device 1.

FIG. 26 shows a third fitness graphical interface 153 being displayed on the graphic display panel 48 of the wireless mobile device 4. The third fitness graphical interface 153 may monitor exercise information regarding both the human 68 and the animal 3 in real-time when both the animal 3 and the human 68 are performing a tandem exercise routine. It may provide buttons such as a start/pause button 102 to allow the human 68 to begin or pause the tandem exercise routine. It may also include a "done" button 103 that ends the tandem exercise routine. During the animal's 3 exercise routine, the third fitness graphical interface 153 may provide statistics regarding the animal's 3 performance and the human's 68 performance in a tandem exercise data array 104. The tandem exercise data array 104 may include statistics and information regarding the tandem exercise routine, such as the time elapsed and the activity being performed (e.g., running, biking, hiking or walking), the distance traveled, the current pace, the average pace, the heart rate, the percentage of heart rate relative to maximum heart rate, the calories burned and the exercise level for both the animal 3 and the human 68. The third fitness graphical interface 153 may also include a message field 105 that may provide warnings or progress reports on either or both of the animal 3 or the human 68. For example, messages in the message field 105 may include recommendations generated by software in the "Fitness" application that analyzes some or all the statistics in the tandem exercise data array 104 and/or the input fields from the first fitness graphical interface 151 and outputs a message to advise the human 68 as to when the training level needs adjustment in order to maintain a desired heart rate, calorie burn or other benchmark fitness criteria.

The third fitness graphical interface 153 may also include the connected device indicator 51 to indicate the animal-worn device 1 that has been selected. It may include the status indicator 50 that indicates the status of the connection between the wireless mobile device 4 and the animal-worn device 1. It may also include the battery level indicator 55 that graphically displays the battery charge level of the animal-worn device 1.

Figure 27:
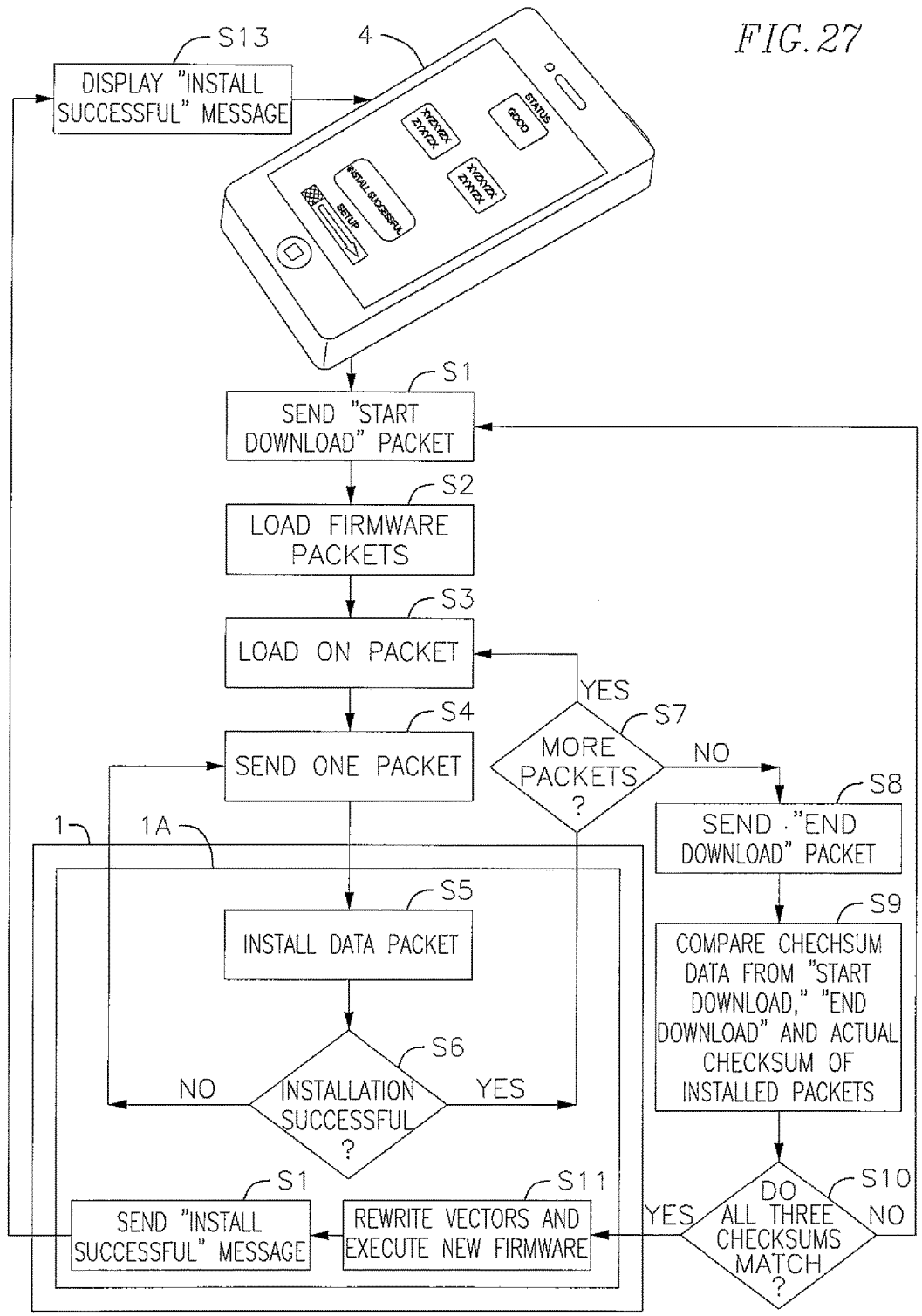
FIG. 27 is a block diagram of a firmware upload from the wireless mobile device to the animal-worn device.

FIG. 27 is a block diagram of a firmware upload from the wireless mobile device 4 to the animal-worn device 1. The embodiments described above may use the approach described in FIG. 27 to load and update firmware from the wireless mobile device 4 to the animal-worn device 1 to avoid potential firmware update issues that may occur when updating the animal-worn device 1 through the wireless mobile device 4. When using a wireless protocol, such as BLUETOOTH low energy BLE, with its characteristically low data rate and limited range, using a conventional boot loader program to upgrade firmware wirelessly can be inconvenient and risky. The lengthy time required to slowly pass kilobytes of data by such conventional means could render the animal-worn receiver 1 unusable for a significant time. Additionally, signal loss or power loss could cause the firmware download to halt or be corrupted, requiring a restart of the entire firmware upgrade process. This problem can be addressed by maintaining two isolated sections of program memory in the animal-worn device's 1 main processor, one for the current firmware which may continue to run throughout the upgrade process, and another in which the new firmware version is to be loaded. This allows the animal worn transceiver 1 to keep performing all its functions of running the current firmware while the new firmware is slowly transmitted over the wireless link. When the download is complete, the animal worn transceiver's 1 processor overwrites startup and interrupt vectors to point to the new firmware. If ever the new firmware is unstable, boot loader software in the animal-worn device's 1 processor can be configured to detect the fault and switch back to the previous firmware version by rewriting the previous vectors. Multiple upgrades of the firmware may be accommodated by placing the succeeding version in a currently unused block of program memory, always preserving the latest versions of firmware.

As shown in FIG. 27, data regarding the firmware is loaded on the wireless mobile device 4 (82) and then individual packets of firmware are loaded (S3) and sent (S4) to the animal-worn device 1. Such packets may be transmitted, for example, using BLUETOOTH 4.0 BLE. Each packet of data has a length (in this example the length is 20 bytes but other lengths are possible) and may include a message identifier code, a ROM address of the first byte of code in the packet, the number of firmware bytes in the packet—for example, from 1 to 15 bytes—and the actual bytes of data. Boot loader software in the animal-worn device's processor 1A installs each packet of firmware (S5) into the processor's 1A internal Flash ROM, starting at an included starting address. If every byte is successfully installed, the boot loader software sends an acknowledgement message requesting the next bytes (S6, S3). If not, it sends a message requesting the previous data (S6, S4). The boot loader software may specify any starting address for the next 15 firmware bytes, thus allowing for reprogramming of an entire block of ROM should an earlier written byte of data be erased, for example during a power failure. This robustness also allows for the fixing or adjusting of code errors to a great degree without sending an entire new firmware file.

Prior to starting the firmware download, a unique "start download" data packet is sent by the wireless mobile device 4 (S1) and received at the animal-worn device 1 indicating the start of the firmware upgrade. The "start download" packet specifies the total number of firmware bytes to be transferred and a checksum of all the bytes to be transferred. Subsequent to the last byte of firmware being downloaded, and when there are no additional packets to be transferred (S7), a unique "end download" packet is sent by the wireless mobile device 4 (S8) with the checksum again included. The animal-worn device's 1 processor compares the starting checksum to the ending checksum and the actual checksum of all the bytes loaded into ROM memory (S10). If all three checksums match, the upgrade is deemed successful and the vectors are rewritten to start execution of the new firmware (S11). The boot loader software may send a "success" (S12) or "failed" (S10, S1) message to the wireless mobile device 4. If successful, a "Install Successful" message can be displayed on the wireless mobile device's 4 display screen (S13). If the installation fails, the wireless mobile device 4 may repeat the upgrade process a predetermined number of times (S10, S1) before displaying a failed status message on the wireless mobile device's 4 display screen and halting the firmware upgrade process.

While the present invention has been described in connection with certain exemplary embodiments, it is to be understood that the invention is not limited to the disclosed embodiments, but is instead intended to cover various modifications and equivalent arrangements included within the spirit and scope of the of the appended claims, and equivalents thereof.

What is claimed is:

1. A method for updating firmware in an animal worn device on a wireless system comprising:
providing an animal worn device for training an animal having a housing, one or more inputs and one or more outputs for controlling the animal, a processor located within the housing containing the firmware having an instruction set consisting of digital operating code for controlling how a wireless mobile device manipulates the one or more inputs or outputs, and a transceiver for communicating with the wireless mobile device;
providing a preprogrammed computer application configured to run on the wireless mobile device;
locating and downloading an external new firmware code file from a server to the wireless mobile device based upon data received from the animal worn device for training the animal;
wirelessly transferring the entire new firmware code file via the transceiver to the animal worn device for training the animal thereby updating the instruction set thus modifying how the inputs or outputs are manipulated; and
wherein the transferring is made over a direct wireless link between the animal worn device for training the animal and the wireless mobile device via a low energy protocol in the absence of a physical connection, signal relay or network relay verifying that the new firmware code file has been transferred correctly and installing the entire new firmware code file once the new firmware code file has been verified;
wherein an original firmware code file residing in the animal worn device for training the animal is preserved and operable;
wherein the processor further contains software to detect a fault in operation of the new firmware code file and wherein the processor reverts to use of the original firmware code file should a fault be detected at a time after installation of the new firmware code file; and
wherein the new firmware code file controls two or more operations of the animal worn device including:
activation of at least one output for applying stimulus to the animal in response to detection of a radio field emitted by a wire loop antenna surrounding the animal;
activation of at least one output in response to a command received from the wireless mobile device;
activation of at least one output to apply stimulus to the animal in response to detection by the animal worn device of an utterance emitted by the animal wherein the output is activated by the animal worn device without a command received by the wireless mobile device;
wireless control by the animal worn device of an external apparatus or wireless control of the animal worn device by an external apparatus;
activation of at least one output to apply stimulus to the animal when detection of a continuous signal from the wireless mobile device falls below a preset signal level; and
sending data from an input to the wireless mobile device wherein the wireless mobile device displays the physical activity of the animal based on the input data.

2. The method of claim 1, wherein the new firmware file is transferred to a first electronic location in a processor in the animal worn device for the animal, said first electronic location being separate from a second electronic location in the processor wherein a current firmware file is located.

3. The method of claim 2, further comprising:
running the processor on a current instruction set of a current firmware file, and
switching the processor from running on the current instruction set to running on a new instruction set of the new firmware file while keeping the current firmware file intact.

4. The method of claim 1, further comprising:
sending an initial checksum of all data bytes contained in the new firmware file from the mobile device to the animal worn device for the animal prior to transferring the new firmware file,
sending a final checksum of all data bytes contained in the new firmware file from the wireless mobile device to the animal worn device for the animal after transferring of the new firmware file,
calculating at the animal worn device for the animal an actual checksum of all data bytes received by the device for the animal for the new firmware file;
comparing the initial checksum, the actual checksum and the final checksum; and
running the new firmware file if the initial checksum, the actual checksum and the final checksum are identical.

5. The method of claim 1, further comprising restructuring the new firmware at the server based upon information received from the animal worn device.

6. The method of claim 1, further comprising sending messages from the server to the animal worn device for the animal.

7. The method of claim 1, further comprising sending messages from the server to the wireless mobile device.

8. The method of claim 1, further comprising sending input data from the animal worn device for the animal to an external device in real time.

9. The method of claim 8 wherein the external device is the mobile device.

10. The method of claim 8 wherein the external device is the server.

11. The method of claim 8 wherein the external device is a router.

12. The method of claim 8 wherein the external device is an internet server.

13. A method for updating firmware on a wireless animal training system for an animal comprising:
providing an animal worn device for training an animal having a housing, one or more inputs or one or more outputs for controlling the animal, a processor located within the housing containing firmware consisting of an instruction set of digital operating code for controlling how the wireless mobile device manipulates the one or more outputs and digital operating code capable of activating outputs at the device for training the animal independent of the wireless mobile device, and a single transceiver for communicating with the wireless mobile device, said transceiver operating a low energy protocol;
providing a preprogrammed computer application configured to run on the mobile device;
locating and downloading an external new firmware code file from a server to the wireless mobile device; and
wirelessly transferring the new firmware code file via the low energy protocol by the transceiver to the device for training the animal;
wherein the transferring is made over a direct wireless link between the animal worn device for training the animal and the wireless mobile device in the absence of a physical connection, signal relay or network relay
verifying that the new firmware code file has been transferred correctly and installing the entire new firmware code file once the new firmware code file has been verified; and
wherein an original firmware code file residing in the animal worn device for training an animal is preserved and operable;
wherein the new firmware code file controls two or more operations of the animal worn device including:
activation of at least one output for applying stimulus to the animal in response to detection of a radio field emitted by a wire loop antenna surrounding the animal;
activation of at least one output in response to a command received from the wireless mobile device;
activation of at least one output to apply stimulus to the animal in response to detection by the animal worn device of an utterance emitted by the animal wherein the output is activated by the animal worn device without a command received by the wireless mobile device;
wireless control by the animal worn device of an external apparatus or wireless control of the animal worn device by an external apparatus;
activation of at least one output to apply stimulus to the animal when detection of a continuous signal from the wireless mobile device falls below a preset signal level; and
sending data from an input to the wireless mobile device wherein the wireless mobile device displays the physical activity of the animal based on the input data.

14. The method of claim 13, wherein the new firmware file is transferred to a first electronic location in a processor in the device for the animal, said first electronic location being separate from a second electronic location in the processor wherein a current firmware file is located.

15. The method of claim 14, further comprising:
running the processor on a current instruction set of a current firmware file, and switching the processor from running on the current instruction set to running on a new instruction set of the new firmware file while keeping the current firmware file intact.

16. The method of claim 13, further comprising:
sending an initial checksum of all data bytes contained in the new firmware file from the mobile device to the device for the animal prior to transferring the new firmware file,
sending a final checksum of all data bytes contained in the new firmware file from the wireless mobile device to the device for the animal after transferring of the new firmware file,
calculating at the device for the animal an actual checksum of all data bytes received by the device for the animal for the new firmware file;
comparing the initial checksum, the actual checksum and the final checksum; and
running the new firmware file if the initial checksum, the actual checksum and the final checksum are identical.

17. The method of claim 13, further comprising restructuring the new firmware at the server based upon information received from the animal device.

18. The method of claim 13, further comprising sending messages from the server to the device for the animal.

19. The method of claim 13, further comprising sending messages from the server to the wireless mobile device.

20. The method of claim 13, further comprising sending input data from the device for the animal to an external device in real time.

21. The method of claim 20 wherein the external device is the mobile device.

22. The method of claim 20 wherein the external device is the server.

23. The method of claim 20 wherein the external device is a router.

24. The method of claim 20 wherein the external device is an internet server.

* * * * *